United States Patent
Waller et al.

(10) Patent No.: US 12,098,180 B2
(45) Date of Patent: Sep. 24, 2024

(54) COMPOSITIONS AND USES OF VASOACTIVE INTESTINAL PEPTIDE (VIP) ANTAGONISTS

(71) Applicant: EMORY UNIVERSITY, Atlanta, GA (US)

(72) Inventors: Edmund K. Waller, Atlanta, GA (US); Yiwen Li, Atlanta, GA (US); Sruthi Ravindranathan, Atlanta, GA (US); Jian-Ming Li, Atlanta, GA (US)

(73) Assignee: Emory University, Atlanta, GA (US)

( * ) Notice: Subject to any disclaimer, the term of this patent is extended or adjusted under 35 U.S.C. 154(b) by 489 days.

(21) Appl. No.: 17/294,248

(22) PCT Filed: Nov. 15, 2019

(86) PCT No.: PCT/US2019/061760
§ 371 (c)(1),
(2) Date: May 14, 2021

(87) PCT Pub. No.: WO2020/102694
PCT Pub. Date: May 22, 2020

(65) Prior Publication Data
US 2022/0002372 A1 Jan. 6, 2022

Related U.S. Application Data

(60) Provisional application No. 62/768,060, filed on Nov. 15, 2018.

(51) Int. Cl.
*C07K 14/575* (2006.01)
*C12N 5/0783* (2010.01)
*A61K 38/00* (2006.01)

(52) U.S. Cl.
CPC ...... *C07K 14/57563* (2013.01); *C12N 5/0638* (2013.01); *A61K 38/00* (2013.01); *C12N 2501/35* (2013.01); *C12N 2501/515* (2013.01)

(58) Field of Classification Search
CPC ............ C07K 14/57563; C12N 5/0638; C12N 2501/35; C12N 2501/515; A61K 38/00
See application file for complete search history.

(56) References Cited

U.S. PATENT DOCUMENTS

| | | | |
|---|---|---|---|
| 5,217,953 A | 6/1993 | Gozes et al. | |
| 5,565,424 A | 10/1996 | Gozes et al. | |
| 6,630,124 B1 * | 10/2003 | Gozes | A61P 35/00 424/9.1 |
| 2009/0093408 A1 | 4/2009 | Bridon et al. | |
| 2017/0258904 A1 | 9/2017 | Waller et al. | |

FOREIGN PATENT DOCUMENTS

| | | |
|---|---|---|
| JP | H09511494 | 11/1997 |
| JP | H1067676 A | 3/1998 |
| JP | 2003530297 | 10/2003 |
| WO | 9521194 A1 | 8/1995 |
| WO | 2017176932 A1 | 10/2017 |

OTHER PUBLICATIONS

Terry W. Moody, VIP/PACAP, and their receptors and cancer, Curr Opin Endocrinol Diabetes Obes. Feb. 2016 ; 23(1): 38-47.*
Agrawal, Y. P., et al. "Cell-cycle kinetics and VSV-G pseudotyped retrovirus-mediated gene transfer in blood-derived CD34+ cells." Experimental hematology 24.6 (1996): 738-747.
Almquist, Ronald G., et al. "Synthesis and biological activity of a ketomethylene analog of a tripeptide inhibitor of angiotensin converting enzyme." Journal of medicinal chemistry 23.12 (1980): 1392-1398.
Alvarez, Ronald D., and David T. Curiel. "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients. University of Alabama Comprehensive Cancer Center, Birmingham, AL." Human gene therapy 8.5 (1997): 597-613.
Asahara, Haruichi, and Shaorong Chong. "In vitro genetic reconstruction of bacterial transcription initiation by coupled synthesis and detection of RNA polymerase holoenzyme." Nucleic acids research 38.13 (2010): e141-e141.
Bagshawe, K. D. "Towards generating cytotoxic agents at cancer sites. The First Bagshawe Lecture." Br. J. Cancer 60 (1989): 275-281.
Bagshawe, K. D., et al. "A cytotoxic agent can be generated selectively at cancer sites." British journal of cancer 58.6 (1988): 700-703.
Banerji, Julian, Laura Olson, and Walter Schaffner. "A lymphocyte-specific cellular enhancer is located downstream of the joining region in immunoglobulin heavy chain genes." Cell 33.3 (1983): 729-740.
Battelli, M. G., et al. "T lymphocyte killing by a xanthine-oxidase-containing immunotoxin." Cancer Immunology, Immunotherapy 35.6 (1992): 421-425.
Brown, Valerie I., and Mark I. Greene. "Molecular and cellular mechanisms of receptor-mediated endocytosis." DNA and cell biology 10.6 (1991): 399-409.

(Continued)

*Primary Examiner* — Julie Ha
*Assistant Examiner* — Erinne R Dabkowski
(74) *Attorney, Agent, or Firm* — Meunier Carlin & Curfman LLC

(57) ABSTRACT

This disclosure relates to VIP antagonist for uses in managing the treatment or prevention of cancer and viral infections. In certain embodiments, this disclosure relates to chimeric variants of VIP antagonists, as peptides disclosed herein, and pharmaceutical composition comprising the same. In certain embodiments, this disclosure contemplates methods of stimulating immune cells to target cancer by mixing immune cells in vitro with peptides disclosed herein and further administering an effective amount of stimulated immune cells to a subject in need of cancer treatment.

6 Claims, 6 Drawing Sheets
Specification includes a Sequence Listing.

(56) References Cited

OTHER PUBLICATIONS

Crystal, Ronald G., et al. "Phase I Study of Direct Administration of a Replication Deficient Adenovirus Vector Containing the E. coli Cytosine Deaminase Gene to Metastatic Colon Carcinoma of the Liver in Association with the Oral Administration of the Pro-Drug 5-Fluorocytosine. The New York Hospital—Cornell Medical Center, New York, NY." Human gene therapy 8.8 (1997): 985-1001.
Goodman, Stacey, et al. "Recombinant adeno-associated virus-mediated gene transfer into hematopoietic progenitor cells [published erratum appears in Blood Feb. 1, 1995; 85 (3): 862]." (1994): 1492-1500.
Greenaway, P. J., et al. "Human cytomegalovirus DNA: BamHI, EcoRI and PstI restriction endonuclease cleavage maps." Gene 18.3 (1982): 355-360.
Handbook of Monoclonal Antibodies, Ferrone et al., eds., Noges Publications, Park Ridge, N.J., (1985) ch. 22 and pp. 303-357.
Hann, Michael M., et al. "On the double bond isostere of the peptide bond: preparation of an enkephalin analogue." Journal of the Chemical Society, Perkin Transactions 1 (1982): 307-314.
Holladay, Mark W., and Daniel H. Rich. "Synthesis of hydroxyethylene and ketomethylene dipeptide isosteres." Tetrahedron Letters 24.41 (1983): 4401-4404.
Hruby, Victor J. "Conformational restrictions of biologically active peptides via amino acid side chain groups." Life sciences 31.3 (1982): 189-199.
Hudson, Derek, et al. "Methionine enkephalin and isosteric analogues I. Synthesis on a phenolic resin support." International journal of peptide and protein research 14.3 (1979): 177-185.
Hughes, Brenda J., et al. "Monoclonal antibody targeting of liposomes to mouse lung in vivo." Cancer research 49.22 (1989): 6214-6220.
Jaeger, John A., Douglas H. Turner, and Michael Zuker. "[17] Predicting optimal and suboptimal secondary structure for RNA." (1990): 281-306.
Jaeger, John A., Douglas H. Turner, and Michael Zuker. "Improved predictions of secondary structures for RNA." Proceedings of the National Academy of Sciences 86.20 (1989): 7706-7710.
Jennings-White et al. "Synthesis of ketomethylene analogs of dipeptides", Tetrahedron Lett 23:2533 (1982).
Laimins, L. A., D. B. Rhoads, and W. Epstein. "Osmotic control of kdp operon expression in Escherichia coli." Proceedings of the National Academy of Sciences 78.1 (1981): 464-468.
Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.
Litzinger, David C., and Leaf Huang. "Biodistribution and immunotargetability of ganglioside-stabilized dioleoylphosphatidylethanolamine liposomes." Biochimica et Biophysica Acta (BBA)-Biomembranes 1104.1 (1992): 179-187.
Lusky, M. O. N. I. K. A., et al. "Bovine papilloma virus contains an activator of gene expression at the distal end of the early transcription unit." Molecular and Cellular Biology 3.6 (1983): 1108-1122.
Miller, A. Dusty, and C. A. R. O. L. Buttimore. "Redesign of retrovirus packaging cell lines to avoid recombination leading to helper virus production." Molecular and Cellular Biology 6.8 (1986): 2895-2902.
Mitani, Kohnoske, Frank L. Graham, and C. Thomas Caskey. "Transduction of human bone marrow by adenoviral vector." Human gene therapy 5.8 (1994): 941-948.
Morley, J. S. "Modulation of the action of regulatory peptides by structural modification." Trends in Pharmacological Sciences 1.2 (1980): 463-468.
Mulligan, R. C., and P. Berg. "Expression of a bacterial gene in mammalian cells." Science 209.4463 (1980): 1422-1427.

Naldini, Luigi, et al. "In vivo gene delivery and stable transduction of nondividing cells by a lentiviral vector." Science 272.5259 (1996): 263-267.
Needleman, Saul B., and Christian D. Wunsch. "A general method applicable to the search for similarities in the amino acid sequence of two proteins." Journal of molecular biology 48.3 (1970): 443-453.
Osborne, Timothy F., et al. "Transcription control region within the protein-coding portion of adenovirus E1A genes." Molecular and cellular biology 4.7 (1984): 1293-1305.
Pastan, Ira, et al. "A retrovirus carrying an MDR1 cDNA confers multidrug resistance and polarized expression of P-glycoprotein in MDCK cells." Proceedings of the National Academy of Sciences 85.12 (1988): 4486-4490.
Pearson, William R., and David J. Lipman. "Improved tools for biological sequence comparison." Proceedings of the National Academy of Sciences 85.8 (1988): 2444-2448.
Petersen, Christopher T., et al. "Improving T-cell expansion and function for adoptive T-cell therapy using ex vivo treatment with PI3Kδ inhibitors and VIP antagonists." Blood advances 2.3 (2018): 210-223.
Petersen, Christopher T., Jian-Ming Li, and Edmund K. Waller. "Administration of a vasoactive intestinal peptide antagonist enhances the autologous anti-leukemia T cell response in murine models of acute leukemia." OncoImmunology 6.5 (2017): e1304336.
Pietersz, Geoffrey A., and Ian FC McKenzie. "Antibody conjugates for the treatment of cancer." Immunological reviews 129.1 (1992): 57-80.
Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.
Schwarzenberger, Paul, et al. "Targeted gene transfer to human hematopoietic progenitor cell lines through the c-kit receptor." (1996): 472-478.
Senter, Peter D., et al. "Generation of 5-fluorouracil from 5-fluorocytosine by monoclonal antibody-cytosine deaminase conjugates." Bioconjugate chemistry 2.6 (1991): 447-451.
Senter, Peter D., et al. "Generation of cytotoxic agents by targeted enzymes." Bioconjugate chemistry 4.1 (1993): 3-9.
Shimizu, Yoshihiro, et al. "Cell-free translation reconstituted with purified components." Nature biotechnology 19.8 (2001): 751-755.
Smith et al., Antibodies in Human Diagnosis and Therapy, Haber et al., eds., Raven Press, New York (1977) pp. 365-389.
Smith, Temple F., and Michael S. Waterman. "Comparison of biosequences." Advances in applied mathematics 2.4 (1981): 482-489.
Southern, P. J., and P. Berg. "Transformation of mammalian cells to antibiotic resistance with a bacterial gene under control of the SV40 early region promoter." Journal of molecular and applied genetics 1.4 (1982): 327-341.
Spatola, Arno F., et al. "Structure-activity relationships of enkephalins containing serially replaced thiomethylene amide bond surrogates." Life sciences 38.14 (1986): 1243-1249.
Sugden, Bill, K. A. T. H. Y. Marsh, and J. O. H. N. Yates. "A vector that replicates as a plasmid and can be efficiently selected in B-lymphoblasts transformed by Epstein-Barr virus." Molecular and cellular biology 5.2 (1985): 410-413.
T.E. Creighton, Proteins: Structure and Molecular Properties, W. H. Freeman & Co., San Francisco pp. 88, 1983.
Zuker, Michael. "On finding all suboptimal foldings of an RNA molecule." Science 244.4900 (1989): 48-52.
Extended European Search Report issued in EP 19885139.6, mailed Aug. 26, 2022.
English translation of Notice of Reasons of Rejection issued in Japanese application No. 2021-527094, mailed Nov. 14, 2023.
International Search Report and Written Opinion for International Application No. PCT/US2019/061760 dated Apr. 1, 2020.

* cited by examiner

```
VIPhyb   KPRRPYTDNYTRLRKQMAVKKYLNSILN  (SEQ ID NO: 1)
VIP      HSDAVFTDNYTRLRKQMAVKKYLNSILN  (SEQ ID NO: 2)
             |                      |
             125                    152

T131A
ANT-1    KPRRPYADNYTRLRKQMAVKKYLNSILN  (SEQ ID NO: 3)

D132V
ANT-2    KPRRPYTVNYTRLRKQMAVKKYLNSILN  (SEQ ID NO: 4)

Y134C
ANT-3    KPRRPYTDNCTRLRKQMAVKKYLNSILN  (SEQ ID NO: 5)

R136S
ANT-4    KPRRPYTDNYTSLRKQMAVKKYLNSILN  (SEQ ID NO: 6)

M141I
ANT-5    KPRRPYTDNYTRLRKQIAVKKYLNSILN  (SEQ ID NO: 7)

K144N
ANT-6    KPRRPYTDNYTRLRKQMAVNKYLNSILN  (SEQ ID NO: 8)

L147M
ANT-7    KPRRPYTDNYTRLRKQMAVKKYMNSILN  (SEQ ID NO: 9)

S149L
ANT-8    KPRRPYTDNYTRLRKQMAVKKYLNLILN  (SEQ ID NO: 10)
```

FIG. 1

COMPOSITIONS AND USES OF VASOACTIVE INTESTINAL PEPTIDE (VIP) ANTAGONISTS

CROSS-REFERENCE TO RELATED APPLICATIONS

This application is a national stage application filed under 35 U.S.C. § 371 of PCT/US2019/061760 filed Nov. 15, 2019, which claims the benefit of U.S. Provisional Application No. 62/768,060 filed Nov. 15, 2018. The entirety of these applications are hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18223PCT_ST25.txt. The text file is 12 KB, was created on Nov. 15, 2019 and is being submitted electronically via EFSWeb.

BACKGROUND

Vasoactive intestinal peptide (VIP) is produced in a variety of cells, including immune cells, neurons, and endocrine cells in the central nervous system. As endogenous VIP is present in nerves of airway smooth muscle and pulmonary vessels within lungs, VIP functions as a bronchodilator. VIP also has the ability to alter cellular proliferation and the production of inflammatory signals through the VIP receptors VPAC1 and VPAC2. A chimeric peptide, referred to as VIPhyb, was developed having a N-terminal sequence which provides membrane permeability followed by the C-terminal 22 amino acid sequence of VIP. As six N-terminal amino acids of native VIP were replaced, VIPhyb has altered biological activity acting as a VIP antagonist. VIP antagonists are also reported in U.S. Pat. Nos. 6,630,124 and 5,217,953.

Traditionally cancer treatments typically utilize surgery, chemotherapy, and radiation therapy. However, alternative methods of strengthen the immune system to attack cancerous cells are reported. These methods include collecting, amplifying, and altering T cells in order to target and stimulate the immune system to aggressively eliminate cancerous cells. In chimeric antigen receptor (CAR) T cell therapy, isolated T cell are engineered to express chimeric protein and are administered back into the patient. However, there is a need to identify improved therapies.

Petersen et al. report administration of VIPhyb enhances the autologous anti-leukemia T cell response in murine models of acute leukemia. Oncoimmunology, 2017, 6(5): e1304336. Petersen et al. report improving T-cell expansion and function for adoptive T-cell therapy using ex vivo treatment with PI3Kδ inhibitors and VIP antagonists. Blood Adv. 2018, 2(3):210-223. References cited herein are not an admission of prior art.

SUMMARY

This disclosure relates to VIP antagonist for uses in managing the treatment or prevention of cancer and viral infections. In certain embodiments, this disclosure relates to chimeric variants of VIP antagonists, as peptides disclosed herein, and pharmaceutical composition comprising the same. In certain embodiments, this disclosure contemplates methods of stimulating immune cells to target cancer by mixing immune cells in vitro with peptides disclosed herein and further administering an effective amount of stimulated immune cells to a subject in need of cancer treatment.

In certain embodiments the VIP antagonist is a peptide comprising K P R R P Y $X^1$ $X^2$ N $X^3$ T $X^4$ L R K Q $X^5$ A V $X^6$ K Y $X^7$N $X^8$ I L N (SEQ ID NO: 11), wherein $X^1$ is A or any amino acid; $X^2$ is V or any amino acid; $X^3$ is C or any amino acid; $X^4$ is S or any amino acid; $X^5$ is I or any amino acid; $X^6$ is N or any amino acid; $X^7$ is M or any amino acid; $X^8$ is I or any amino acid; and provided that the peptide is not KPRRPYTDNYTRLRKQMAVKKYLNSILN (SEQ ID NO: 1) or the combination wherein $X^1$ is T, $X^2$ is D, $X^3$ is Y, $X^4$ is R, $X^5$ is M, $X^6$ is K, $X^7$ is L, and $X^8$ is S.

In certain embodiments, the peptide comprises or consists of K P R R P Y $X^1$ $X^2$ N $X^3$ T $X^4$ L R K Q $X^5$ A V $X^6$ K Y N $X^8$ I L N (SEQ ID NO: 11), wherein $X^1$ is A or T, wherein $X^1$ is T only if $X^2$ is V, $X^3$ is C, $X^4$ is S, $X^5$ is I, $X^6$ is N, $X^7$ is M, or $X^8$ is I; wherein $X^2$ is V or D, wherein $X^2$ is D only if $X^1$ is A, $X^3$ is C, $X^4$ is S, $X^5$ is I, $X^6$ is N, $X^7$ is M, or $X^8$ is I; wherein $X^3$ is C or Y, wherein $X^3$ is Y only if is A, $X^2$ is V, $X^4$ is S, $X^5$ is I, $X^6$ is N, $X^7$ is M, or $X^8$ is I; wherein $X^4$ is S or R, wherein $X^4$ is R only if $X^1$ is A, $X^2$ is V, $X^3$ is C, $X^5$ is I, $X^6$ is N, $X^7$ is M, or $X^8$ is I; wherein $X^5$ is I or M, wherein $X^5$ is M only if $X^1$ is A, $X^2$ is V, $X^3$ is C, $X^4$ is S, $X^6$ is N, $X^7$ is M, or $X^8$ is I; wherein $X^6$ is N or K, wherein $X^6$ is K only if $X^1$ is A, $X^2$ is V, $X^3$ is C, $X^4$ is S, $X^5$ is I, $X^7$ is M, or $X^8$ is I; wherein $X^7$ is M or L, wherein $X^7$ is L only if is A, $X^2$ is V, $X^3$ is C, $X^4$ is S, $X^5$ is I, $X^6$ is N, or $X^8$ is I; and wherein $X^8$ is I or S, wherein $X^8$ is S only if $X^1$ is A, $X^2$ is V, $X^3$ is C, $X^4$ is S, $X^5$ is I, $X^6$ is N, or $X^7$ is M.

In certain embodiments, the peptide comprises or consists of:

```
                                        (SEQ ID NO: 3)
KPRRPYADNYTRLRKQMAVKKYLNSILN, (SEQ ID NO: 4)
KPRRPYTVNYTRLRKQMAVKKYLNSILN, (SEQ ID NO: 5)
KPRRPYTDNCTRLRKQMAVKKYLNSILN, (SEQ ID NO: 6)
KPRRPYTDNYTSLRKQMAVKKYLNSILN, (SEQ ID NO: 7)
KPRRPYTDNYTRLRKQIAVKKYLNSILN, (SEQ ID NO: 8)
KPRRPYTDNYTRLRKQMAVNKYLNSILN, (SEQ ID NO: 9)
KPRRPYTDNYTRLRKQMAVKKYMNSILN,
or (SEQ ID NO: 10)
KPRRPYTDNYTRLRKQMAVKKYLNLILN.
```

In certain embodiments, an amino, carboxyl, hydroxyl, or thiol group in a peptide disclosed herein is substituted. In certain embodiments, the peptide is conjugated to a nanoparticle. In certain embodiments, the disclosure contemplates peptides disclosed herein having a label, e.g., fluorescent or radioactive.

In certain embodiments, this disclosure relates to compositions such as pharmaceutical compositions and cell growth media comprising peptides disclosed herein. In certain embodiments, this disclosure relates to pharmaceutical compositions comprising a peptide disclosed herein and pharmaceutically acceptable excipient. In certain embodiments, the pharmaceutical composition is in the form of a capsule, tablets, pill, powder, or granule. In certain embodiments, the pharmaceutical composition is in the form of a sterilized pH buffered aqueous salt solution. In certain embodiments, the pharmaceutical composition is in the form of a container configured to spray a liquid or sealed container with a propellant.

In certain embodiments, this disclosure relates to nucleic acid encoding a peptide as disclosed herein in operable combination with a promoter. In certain embodiments, this disclosure relates to a recombinant vector comprising the nucleic acid encoding a peptide as disclosed herein in operable combination with a promoter. In certain embodiments, this disclosure relates to an expression system or cell comprising a recombinant vector disclosed herein.

In certain embodiments, this disclosure relates to methods of treating or enhancing the immune response to cancer or treating cancer comprising administering an effective amount of a peptide disclosed herein to subject in need thereof. In certain embodiments, the peptide is administered in combination with another chemotherapy agent.

In certain embodiments, this disclosure relates to methods of augmenting T cell activation and ex vivo expansion comprising mixing T cells with a peptide disclosed herein. In certain embodiments, mixing T cells is in combination with an anti-CD3 antibody and/or anti-CD28 antibody. In certain embodiments, the mixing T cells is in combination with phosphatidylinositol 3-kinase δ (PI3Kδ) inhibitor.

In certain embodiments, this disclosure relates to methods of treating or preventing host verses graft disease in a subject comprising administering an effective amount of a peptide disclosed herein to a subject that is to receive or received transplanted allogeneic tissue or cells.

In certain embodiments, this disclosure relates to methods of treating cancers comprising exposing a subject to radiation and/or administering a chemotherapy agent to the subject; transplanting allogeneic hematopoietic stem cells into the subject; and administering a peptide disclosed herein to the subject.

In certain embodiments, this disclosure relates to methods of managing a viral infection comprising administering an effective amount of a peptide as disclosed herein to a subject in need thereof.

In certain embodiments, the subject is a mammal, typically a human.

BRIEF DESCRIPTION OF THE DRAWINGS

FIG. 1 shows antagonistic peptides that differ in internal amino acids from VIPhyb of SEQ ID NO: 1. Native VIP is SEQ ID NO: 2. The sequences are designated ANT-1 through 8 according to the presence or absence of the internal amino acids (labeled "ANT"). In particular, the ANT-1 has an amino acid T to A substitution at amino acid position seven, SEQ ID NO: 3. The ANT-2 sequence has an amino substitution of D to V at amino acid position number 8, SEQ ID NO: 4. The ANT-3 peptide has an amino acid substitution of Y to C at amino acid position number 10, SEQ ID NO: 5. The ANT-4 has an amino acid substitution R to S at amino acid position 12, SEQ ID NO: 6. The ANT-5 has an amino acid substitution M to I at amino acid position number 17, SEQ ID NO: 7. The ANT-6 has an amino acid substitution K to N at amino acid position 20, SEQ ID NO: 8. The ANT-7 has an amino acid substitution L to M at amino acid position number 23, SEQ ID NO: 9. The ANT-8 has an amino acid substitution S to L at amino acid position number 25, SEQ ID NO: 10.

DETAILED DESCRIPTION

Figure 2:
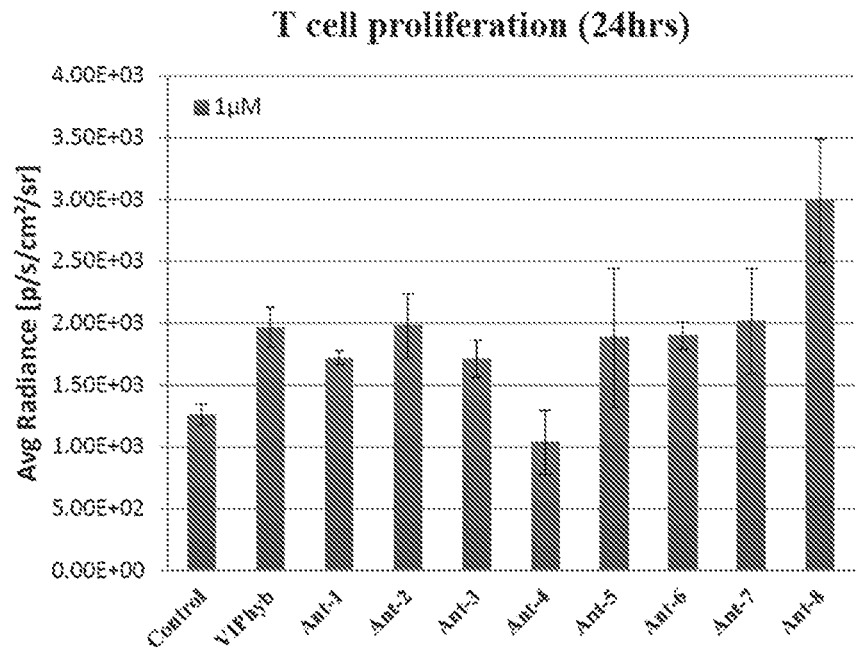
FIG. 2 shows data on T cell proliferation at 24 hr in the presence of the original VIPhyb and Ant 1 through Ant8. T cells from luciferase+C57/BL6 mice were harvested and cultured in 96-well plate with 1 µg/ml anti-CD3 antibody and 30 U/ml IL-2 in the presence of original VIPhyb, Ant-1, Ant-2, Ant-3, Ant-4, Ant-5, Ant-6, Ant-7 or Ant-8 at 1 µM.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The terms "protein" and "peptide" refer to compounds comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

In certain embodiments, the disclosure relates to recombinant peptides comprising sequences disclosed herein or fusions thereof wherein the amino terminal end or the carbon terminal end of the amino acid sequence are optionally attached to a heterologous amino acid sequence, label, or reporter molecule. A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined peptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

As used herein, the term "derivative" refers to a structurally similar peptide that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more peptides linked together by a linking group. It is contemplated that the linking group may be biodegradable. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

In certain embodiments, the peptides discloses herein have at least one non-naturally occurring molecular modification, such as the attachment of polyethylene glycol, the attachment of another peptide resulting in a chimeric peptide, the attachment of a fluorescent dye comprising aromatic groups, fluorescent peptide, a chelating agent capable of binding a radionuclide such as $^{18}F$, N-terminal acetyl, propionyl group, myristoyl and palmitoyl, group or N-terminal methylation, or a C-terminal alkyl ester. In certain embodiments, the disclosure contemplates the disclosure contemplates peptides disclosed herein labeled using commercially available biotinylation reagents. Biotinylated peptide can be used in streptavidin affinity binding, purification, and detection. In certain embodiments, the disclosure contemplates peptide disclose herein containing azide-derivatives of naturally occurring monosaccharides such as N-azidoacetylglucosamine, N-azidoacetylmannosamine, and N-azidoacetylgalactosamine.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amine side chain group such as lysine or an amino acid containing a carboxylic acid side chain group such as aspartic acid or glutamic acid, within the peptide comprising a sequence disclosed herein. In certain embodiments, it is contemplated that the substituent may be covalently bonded through a cysteine in a sequence disclosed herein optionally connected through a linker. In certain embodiments, a substituent is connected through a linker that forms a disulfide with a cysteine amino acid side group.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, $2^{nd}$. Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

The term "prodrug" refers to an agent that is converted into a biologically active form in vivo. Prodrugs are often useful because, in some situations, they may be easier to administer than the parent compound. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto (thiol) group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed peptide or a pharmaceutically acceptable form of the peptide contains a carboxylic acid functional group, a prodrug can comprise a pharmaceutically acceptable ester formed by the replacement of the hydrogen atom of the acid group with a group such as $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as beta-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

If a disclosed peptide or a pharmaceutically acceptable form of the peptide contains an alcohol functional group, a prodrug can be formed by the replacement of the hydrogen atom of the alcohol group with a group such as $(C_1-C_6)$ alkanoyloxymethyl, 1-(($C_1-C_6$)alkanoyloxy) ethyl, 1-methyl-1(($C_1-C_6$)alkanoyloxy)ethyl $(C_1-C_6)$alkoxycarbonyloxymethyl, —N—$(C_1-C_6)$alkoxycarbonylaminomethyl, succinoyl, $(C_1-C_6)$alkanoyl, alpha-amino$(C_1-C_4)$alkanoyl, arylacyl and alpha-aminoacyl, or alpha-aminoacyl-alpha-aminoacyl, where each alpha-aminoacyl group is independently selected from naturally occurring L-amino acids $P(O)(OH)_2$, —$P(O)(O(C_1-C_6)$alkyl$)_2$, and glycosyl (the radical resulting from the removal of a hydroxyl group of the hemiacetal form of a carbohydrate).

If a disclosed peptide or a pharmaceutically acceptable form of the peptide incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, a natural alpha-aminoacyl, —C(OH)C(O)OY$_1$ wherein Y$^1$ is H, $(C_1-C_6)$alkyl or benzyl, —C(OY$_2$)Y$_3$ wherein Y$_2$ is $(C_1-C_4)$ alkyl and Y$_3$ is $(C_1-C_6)$alkyl, carboxy$(C_1-C_6)$alkyl, amino$(C_1-C_4)$alkyl or mono-Nor di-N,N—$(C_1-C_6)$alkylaminoalkyl, —C(Y$_4$)Y$_5$ wherein Y$_4$ is H or methyl and Y$_5$ is mono-N— or di-N,N—$(C_1-C_6)$alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —$C(Hal)R_m$—, —C(Hal)(Hal)-, —C(Hal)H—, —$C(N_3)R_m$—, —$C(CN)R_m$—, —C(CN)(CN)—, —C(CN)H—, —$C(N_3)(N_3)$—, —$C(N_3)$H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100, or 50, or 25, or 10. Examples of linking groups include bridging alkyl groups and alkoxyalkyl groups. Linking groups may be substituted with one or more substituents.

The term "nucleic acid" refers to a polymer of nucleotides, or a polynucleotide. The term is used to designate a single molecule, or a collection of molecules. Nucleic acids may be single stranded or double stranded, and may include coding regions and regions of various control elements, as described below.

The terms "a nucleic acid sequence encoding" a specified peptide refers to a nucleic acid sequence comprising the coding region of peptide or in other words the nucleic acid sequence that encodes peptide product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region if needed to permit proper initiation of transcription and/or correct processing of the primary RNA transcript. Alternatively, the coding region utilized in expression vectors may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genitourinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, pheochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules or derivatives such as alemtuzumab, trastuzumab, ibritumomab tiuxetan, brentuximab vedotin, temozolomide, ado-trastuzumab emtansine, denileukin diftitox, blinatumomab, interferon alpha, aldesleukin, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin, rituximab, and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

In certain embodiments, treatment of cancer may be combined with another anticancer agent. In certain embodiments, the anti-cancer agent is selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof.

In certain embodiments, the method of administration is in a subject with a lymphodepleted environment. In certain embodiments, lymphodepleting agents are cyclophosphamide and fludarabine.

As used herein the term "idelalisib" refers to the compound (S)-2-(1-(9H-purin-6-ylamino)propyl)-5-fluoro-3-phenylquinazolin-4(3H)-one or alternative salts thereof.

As used herein, "T cells that are negative for CD28 and/or CD27" refers to having low expression or lack expression of relative concentrations of these markers when compared to normal T-cells that express CD3 surface antigen markers in a healthy subject.

The term "fluorescence-activated cell sorting" or "FACS" refers to a method of sorting a mixture of cells into two or more areas, typically one cell at a time, based upon the fluorescent characteristics of each cell, a respectively applied electrical charge, and separation by movement through an electrostatic field. Typically, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. The stream is then returned to neutral after the droplet breaks off. In other systems, a charge is provided on a conduit inducing an opposite charge on the droplet. Cells are typically made fluorescent by mixing the cell with antibody that specifically binds a marker that is made fluorescent by conjugation to a fluorescent molecule. However, other methods of making a cell fluorescent are contemplated such as by the use of molecular beacons.

A "minimal essential medium" refers to a medium containing salts of calcium, magnesium, potassium, sodium, phosphate, and bicarbonate, vitamins, and essential amino acids. The 12 essential amino acids are: L-arginine; L-cystine; L-glutamine; L-histidine; L-isoleucine; L-leucine; L-methionine; L-phenylalanine; L-threonine; L-tryptophan; L-tyrosine; and L-valine. An MEM is often supplemented with components such as bicarbonate or glutamine. In certain embodiments, this disclosure contemplates a minimal essential medium supplemented with non-essential amino acids: L-ala; L-asn; L-asp; L-glu; L-gly; L-pro and L-ser. In certain embodiments, this disclosure contemplates a minimal essential medium supplemented with nucleosides (ribonucleosides and/or deoxyribonucleosides).

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule. The term recombinant nucleic acid is distinguished from the natural recombinants that result from crossing-over between homologous chromosomes. Recombinant nucleic acids as used herein are an unnatural union of nucleic acids from non-homologous sources, usually from different organisms.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "vasoactive intestinal peptide" and "VIP" refer to (SEQ ID NO: 2) HSDAVFTDNYTRLRKQMAVK-KYLNSILN unless the context suggests otherwise. VIP is a multifunctional endogenous polypeptide that modulates both innate and adaptive immunity at multiple levels of immune cell differentiation and activation. VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors—VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Compositions

In certain embodiments, the disclosure contemplates pharmaceutical composition comprising peptide disclosed herein, or nanoparticle thereof, or optionally other pharmaceutical agent, or pharmaceutically acceptable salts thereof, and a pharmaceutically acceptable excipient.

In certain embodiments, this disclosure relates to compositions such as pharmaceutical compositions and cell growth media comprising peptides disclosed herein. In certain embodiments, this disclosure relates to pharmaceutical compositions comprising a peptide disclosed herein and pharmaceutically acceptable excipient. In certain embodiments, the pharmaceutical composition is in the form of a capsule, tablets, pill, powder, or granule. In certain embodiments, the pharmaceutical composition is in the form of a sterilized pH buffered aqueous salt solution. In certain embodiments, the pharmaceutical composition is in the form of a container configured to spray a liquid or sealed container with a propellant.

Effective doses may be extrapolated from dose-response curves derived from in vitro or animal model test systems. For peptides disclosed herein or nanoparticle thereof, or other agents, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of peptides disclosed herein or nanoparticle thereof or agent may be reduced by enhancing uptake and tissue penetration by modifications such as, for example, lipidation and the inclusion of natural or artificial pulmonary surfactants.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, the pharmaceutical composition is in solid form surrounded by an enteric coating, i.e., a polymer barrier applied on oral medication that prevents its dissolution or disintegration in the gastric environment. Compounds typically found in enteric coatings include methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, and combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be both natural and artificial pulmonary surfactants, sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with peptide disclosed herein or nanoparticle thereof or agents disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising peptide disclosed herein or nanoparticle thereof, and agents disclosed herein and pharmaceutically acceptable excipient. In certain embodiments, this disclosure contemplates the production of a medicament comprising peptide disclosed herein, or nanoparticle thereof, or agents disclosed herein and uses for methods disclosed herein.

In certain embodiments, the disclosure relates to pharmaceutical compositions comprising peptide disclosed herein or nanoparticle thereof, and agents disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo), preparations incorporated into pulmonary surfactants (both natural and artificial), and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminium monostearate and gelatin.

Solid dosage forms for oral administration include capsules, tablets, pills, powders and granules. In such solid dosage forms, the peptides disclosed herein or nanoparticle thereof, or agents may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the peptides disclosed herein, or nanoparticle thereof, and agents, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, peptides disclosed herein, or nanoparticle thereof, and agents disclosed herein and a pharmaceutical carrier, are provided already in a combined dry form ready to be reconstituted together. In other embodiments, it is contemplated that peptides disclosed herein or nanoparticle thereof, and optionally agents disclosed herein, and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the peptides disclosed herein, or nanoparticle thereof, or agents can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as inhalers, syringes, vials, tubes, etc. The pharmaceutical composition may then be applied via actuation or specific needles of the syringe or via suitable catheters. A typical diluent comprises water for injection, and NaCl (preferably 50 to 150 mM, especially 110 mM), CaCl2 (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, this disclosure contemplates a kit comprising a pharmaceutical composition disclosed herein such as peptides disclosed herein, or nanoparticle thereof, or agent and a container optionally with a suitable diluent. Further components of the kit may be instructions for use, administration means, such as inhalers, syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

It is contemplated that any of the peptides disclose herein may be modified with hydrocarbon or polyethylene glycol groups in order to provide improve properties such as solubility, bioavailability, and/or biological degradation.

In certain embodiments, this disclosure relates to methods of coupling a peptide disclosed herein to a nanoparticle. In certain embodiments, the nanoparticle is comprised of poloxamer-stabilized polypropylene sulfide. In certain embodiments, the nanoparticle has a diameter of between 10 and 100 nm. In certain embodiments, the nanoparticle has a diameter between 20 and 50 nm, preferably 30 nm.

In certain embodiments, the disclosure contemplates using particles disclosed herein when the peptide sequence couple to the nanoparticle is contains a peptide disclosed herein plus a C-terminal linker peptide, GGGGSC (SEQ ID NO: 15). In certain embodiments, the particle contains the peptide sequence e.g., KPRRPYTDNYTRLRKQMAVK-KYLNLILNGGGGSC (SEQ ID NO: 12). In certain embodiments, the chemical linkage between the peptides disclosed herein and the nanoparticles is a disulfide bond.

In certain embodiments, the pharmaceutically acceptable excipient is aerosolizing agent or phospholipids. In certain embodiments, the aerosolizing agent is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the phospholipid is dipalmitoylphosphatidylcholine, palmitoyl-oleoyl phosphatidylglycerol, phosphatidylglycerol, or combinations thereof.

In certain embodiments, the pharmaceutical compositions may be stored in a nebulizer, inhaler, or other container optionally sealed or under a pressure for propelling the pharmaceutical agent(s). The container may contain a spraying apparatus that is manually actuated or pressurized. Metered dose inhalers (MDIs) typically have a handheld aerosol canister that, upon being pushed, releases an amount of medicine to inhale. Dry powder inhalers (DPIs) do not use a propellant to release the medicine. Instead, a dry powder form of the peptide or nanoparticle thereof or agent is drawn into your lungs after a breath. In certain configurations, a container comprising the peptides disclosed herein or nanoparticle thereof is inserted a device. Pressing a button or section on the device pierces the container. One can breathe in the powder contained in the container through a mouthpiece on the device.

In certain embodiments, the pharmaceutical compositions may contain naturally or non-naturally occurring pulmonary surfactant compositions. Contemplated natural pulmonary surfactant compositions typically comprise 70-90% phospholipids (PC) such as dipalmitoylphosphatidylcholine (DPPC), phosphatidylcholine, and phosphatidylglycerol (PG); and 1-10% surfactant-associated proteins, apolipoproteins SP-A (SFTPA1), B (SFTPB), C (SFTPC) and D (SFTPD) (SP standing for "surfactant-associated protein"); and 1-10% Cholesterol (neutral lipids). Artificial pulmonary surfactants include colfosceril palmitate, a mixture of DPPC with hexadecanol and tyloxapol added as spreading agents; pumactant (Artificial Lung Expanding Compound or ALEC), a mixture of DPPC and PG; KL-4, composed of DPPC, palmitoyl-oleoyl phosphatidylglycerol, and palmitic acid, combined with a 21 amino acid synthetic peptide that mimics the structural characteristics of SP-B; and compositions composed of DPPC, PG, palmitic acid and recombinant SP-C shares a nearly identical sequence with human SP-C except that the palmitoylated cysteines are absent and have been replaced with phenylalanines to eliminate protein oligomerization. Contemplated animal derived surfactants include beractant (Alveofact™), extracted from cow lung lavage fluid and (Survanta™), extracted from minced cow lung with additional DPPC, palmitic acid and tripalmitin; calfactant (Infasurf), extracted from calf lung lavage fluid; and poractant alfa (Curosurf™)—extracted from material derived from minced pig lung.

In certain embodiments, the pharmaceutical compositions disclosed herein further comprise a respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, budesonide, beclomethasone dipropionate, alclometasone dipropionate; a p38 antagonist such as losmapimod; a phosphodiesterase (PDE) inhibitor such as a methylxanthine, theophylline, and aminophylline; a selective PDE isoenzyme inhibitor, a PDE4 inhibitor and the isoform PDE4D, such as tetomilast, roflumilast, oglemilast, ibudilast; a modulator of chemokine receptor function such as maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as licofelone, zileuton, zafirlukast, or montelukast; and a myeloperoxidase antagonist such as resveratrol and piceatannol.

In certain embodiments, the disclosure relates to in vitro cell culture compositions comprising a minimal essential medium and a peptide disclosed herein or nanoparticle thereof Methods of Use In certain embodiments, this disclosure relates to peptides disclosed herein e.g., Ant-8, KPRRPY-TDNYTRLRKQMAVKKYLNLILN (SEQ ID NO: 10), for use in methods of treating cancer. IN certain embodiments, this disclosure contemplates methods of treating cancer comprising administering an effective amount of a peptide disclosed herein optionally in combination with a chemotherapy agent. In certain embodiments, this disclosure relates to methods of treating or enhancing the immune response to cancer using a peptide disclosed herein, optionally conjugated to nanoparticles, in combination with an antibody to immune check-point molecules to a subject in need thereof.

In certain embodiments, the subject is diagnosed with a cancer selected from the group of melanoma, lung cancer, renal cancer, leukemia, non-Hodgkin lymphoma, Hodgkin lymphoma, myeloma, bladder cancer, pancreatic cancer, gastric cancer, esophageal cancer, glioblastoma, colon cancer, breast cancer and prostate cancer.

In certain embodiments, the antibody to an immune check-point molecule is selected from the group of anti-PD1 antibodies including Pembrolizumab (Keytruda™) and Nivolumab (Opdivo™). In certain embodiments, the antibody to immune check-point molecule is selected from the group of anti-PDL1 antibodies including Atezolizumab (Tecentriq™), Avelumab (Bavencio), Durvalumab (Imfinzi™). In certain embodiments, the antibody to immune check-point molecule is Ipilimumab (Yervoy™).

In certain embodiments, the peptide therapeutic is given by intravenous or sub-cutaneous injection. In certain embodiments, the peptide therapeutic is given by inhalation to deliver drug to the pulmonary alveoli. In certain embodiments, the peptide therapeutic is administered to a handheld delivery device driven by compressed gas. In certain embodiments, the peptide therapeutic is dissolved in a solution of sterile saline and administered as an aerosol.

In certain embodiments, it is contemplated that a peptide disclosed herein is used in certain cellular immunotherapies that are effective for treating cancer such as lymphocyte infusions or allogeneic bone marrow transplantations. Donor immune cells, particularly NK cells and T-cells, cells have anti-cancer cytotoxic activity. VIP antagonism of the peptide enhances cellular immune responses in vivo. VIP antagonism increases the cytotoxic activity of antigen-specific T-cells and NK cells. VIP antagonism is predicted to increase the anti-cancer activity of NK cells or antigen-specific T-cells. VIP antagonism in conjunction with cellular immunotherapy is predicted to increase the efficacy of said therapy. It is believed that the absence of VIP does not increase the "off-target" graft versus host disease activity of donor lymphocytes in recipients of allogeneic bone marrow transplantation. Thus, administration of VIP antagonists to subjects with cancer receiving cellular therapies, e.g., donor lymphocyte infusions or allogeneic bone marrow transplantation, will increase the anti-cancer activity of said therapy.

In certain embodiments, the disclosure relates to methods of enhancing the immune response to a cell therapy comprising administering a peptide disclosed herein to a subject in combination with a cell. In certain embodiments, the subject is diagnosed with leukemia or lymphoma. In certain embodiments, the cell is a blood cell, bone marrow cell, leukocyte, T-cell, natural killer cell, a hematopoietic stem cell, a G-CSF mobilized or non-mobilized blood mononuclear cell.

In certain embodiments, the cell is selected from the group consisting of autologous T-cells, allogeneic cells from a HLA matched donor, or allogeneic cells from a HLA mis-matched donor. In certain embodiments, the cell is a bone marrow cell. In certain embodiments, the cell is a blood mononuclear cell comprising/expressing granulocyte colony-stimulating factor. The cell therapy may be conducted with non-mobilized blood mononuclear cells.

In certain embodiments, it is contemplated that a peptide disclosed herein may be administered to subjects before, during, or after a cell-based immunotherapy including the recipient or donor. The immunotherapy may be performed in combinations with chemotherapy and/or a radiation therapy. It is contemplated that peptide may be used in combination with other immune stimulators including, but not limited to, CpG oligonucleotides, granulocyte colony stimulating factor, granulocyte-macrophage colony stimulating factor, interferon alpha, pegylated interferon, interleukin-12, interleukin-2, and pegfilgrastim.

In certain embodiments, this disclosure relates to methods of treating or preventing graft versus host disease in a subject comprising administering an effective amount of a peptide disclosed herein to a subject after a hematopoietic stem cell transplant or a subject that is to receive or received transplanted allogeneic tissue or cells. In certain embodiments, the subject received transplanted allogeneic hematopoietic stem cells. In certain embodiments, the subject received transplanted allogeneic hematopoietic stem cells separated from peripheral blood. In certain embodiments, the subject received chemotherapy to radiation treatments prior to receiving transplanted allogeneic hematopoietic stem cells.

In certain embodiments, the disclosure relates to methods of treating cancer by performing a stem cell transplantation comprising administering a peptide disclosed herein to the subject in combination with transplanting a multipotent hematopoietic stem cell derived from the subject (self) or a donor. The stem cells may be collected from peripheral blood such as cord blood or placenta-derived stem cells or from the bone marrow. To limit the risks of transplanted stem cell rejection or of severe graft-versus-host disease, the donor will typically have the substantially the same human leukocyte antigens (HLA) as the recipient; however, the donor may have mis-matches for certain antigens.

In certain embodiments, the disclosure relates to methods of providing lymphocyte infusions after a hematopoietic progenitor cell transplant to treat a hematologic malignancy (e.g., cancer of the blood or bone marrow, such as leukemia or lymphoma). A transplant recipient is typically infused with lymphocytes obtained in a leukapheresis procedure from the original allogeneic stem cell (hematopoietic progenitor cell) donor.

In certain embodiments, the disclosure relates to extraction of lymphocytes from the blood and expanding in vitro against tumor antigen(s) and optionally exposing the cells with an appropriate stimulatory cytokine and/or a peptide disclosed herein.

In certain embodiments, the disclosure relates to methods of enhancing topical immunotherapies comprising administering a peptide disclosed herein in combination with providing an immune enhancement cream, such as imiquimod, comprising an interferon-producing drug that causes the activation of T-cells.

In certain embodiments, it is contemplated that peptides disclosed herein can be used in combination with adoptive cell therapies. For example, T cells with a naturally occurring reactivity to cancer can be found infiltrated in tumors of the subject. The tumor can be harvested, and these tumor-infiltrating lymphocytes (TIL) can be expanded, or made more effective, in vitro using interleukin-2 (IL-2), anti-CD3 and allo-reactive feeders. These T cells can then be transferred back into the subject along with administration of a VIP antagonist. Before reinfusion, lymphodepletion of the recipient is typically done to eliminate regulatory T cells as well as normal endogenous lymphocytes that compete with the transferred cells. It is also contemplated that the adoptive cell transfer of lymphocytes may be transduced with a vector encoding T cell receptors (TCRs) that recognize a cancer antigen.

In certain embodiments, this disclosure relates to methods of augmenting T-cell activation and ex vivo expansion by co-incubation of human T cells with a nanoparticle containing a small molecule antagonist of VIP signaling. In certain embodiments, the human T cells are activated with anti-CD3 antibody bound to a plate. In certain embodiments, the human T cells are activated in a mixed lymphocyte reaction. In certain embodiments, the human T cells are activated in vitro by co-incubation with tumor-associated antigens. In certain embodiments, the tumor associate antigens are presented on tumor microvesicles. In certain embodiments, the activated human T cells are infused into a human patient with cancer.

In certain embodiments, the activated human T cells are infused into a human patient with cancer. In certain embodiments, the human patient with cancer has leukemia. In certain embodiments, the human patient with cancer has lymphoma. In certain embodiments, the human patient with cancer has multiple myeloma. In certain embodiments, the human patient with cancer has an epithelial cancer. In certain embodiments, the human patient has lung cancer. In certain embodiments, the human patient has breast cancer. In certain embodiments, the human patient has colon cancer. In certain embodiments, the human patient has prostate cancer. In certain embodiments, the human patient has malignant melanoma. In certain embodiments, the human patient has brain cancer.

In certain embodiments, this disclosure relates to methods of treating a subject diagnosed with cancer comprising administering a cell in combination with a peptide disclosed herein to a subject in need thereof. In certain embodiments, the subject is diagnosed with leukemia. In certain embodiments, the subject is diagnosed with lymphoma. In certain embodiments, the cell is a blood mononuclear cell. In certain embodiments, the cell is a bone marrow cell. In certain embodiments, the cell is a leukocyte. In certain embodiments, the cell is a T-cell. In certain embodiments, the cell is a natural killer cell. In certain embodiments, the cell is a hematopoietic stem cell. In certain embodiments, the cell is a G-CSF mobilized blood mononuclear cell. In certain embodiments, the cell is an HLA matched or mis-matched allogeneic cell. In certain embodiments, the cell is syngeneic cell. In certain embodiments, the cell is an autologous cell. In certain embodiments, the peptide has a C-terminal amide and/or is optionally modified with hydrocarbon or polyethylene glycol groups.

In certain embodiments, this disclosure relates to method of treating leukemia comprising administering a peptide disclosed herein to a subject in combination with transplanting hematopoietic stem cells. In certain embodiments, this disclosure relates to methods comprising expanding lymphocytes in vitro providing expanded cells and exposing the expanded cells with a peptide disclosed herein.

In certain embodiments, lymphocytes are extracted from blood or obtained by leukapheresis. In certain embodiments, expanded cells are further exposed to a stimulatory cytokine or an interferon.

In certain embodiments, this disclosure relates to methods of augmenting anti-cancer immune responses by infusion of a peptide disclosed herein or nanoparticle expressing a peptide disclosed herein. In certain embodiments, the activated T-cells are infused into a patient with chronic CMV infection. In certain embodiments, the activated T-cells are infused into a patient with chronic EBV infection. In certain embodiments, the activated T-cells are infused into a patient with chronic BK virus infection. In certain embodiments, the activated T-cells are infused into a patient with chronic adenovirus infection.

In certain embodiments, this disclosure relates to compositions and methods of reversing senescence in T cells by interrupting vasoactive intestinal peptide (VIP) signaling and/or inhibiting phosphatidylinositol-3-kinase (PI3 kinase) inhibitor signaling and uses in managing cancer and chronic viral infections. In certain embodiments, the disclosure contemplates methods of reversing T cell senescence by mixing T cell in vitro with a peptide disclosed herein or nanoparticle comprising a peptide disclosed herein that prevents VIP from interacting with VIP receptors and/or the addition of a PI3 Kinase inhibitor. In certain embodiments, the disclosure contemplates the expansion of senescent T cells by mixing with a PI3 kinase inhibitor, a nanoparticle or peptide disclosed herein, a VIP degrading enzyme, and combinations thereof.

In certain embodiments, the disclosure contemplates methods of stimulating isolated T cells or expanding senescent T cells by in vitro exposure of T cells to antibodies that bind CD3 and/or CD28 in combination with the PI3 kinase inhibitor, idelalisib, a peptide disclosed herein or nanoparticle disclosed herein, a VIP degrading enzyme, and combinations thereof. In certain embodiments, the disclosure contemplates using anti-CD3 and anti-CD28 antibodies or binding agents optionally linked to a solid substrate such as magnetic beads.

In certain embodiments, the disclosure contemplates methods of proliferating T cells that are negative for CD28 and/or CD27 using an in vitro cell culture as disclosed herein providing replicated T cells that have increased expression of CD28 and/or CD27 compared with levels prior to replication.

In certain embodiments, the disclosure contemplates methods of proliferating T cells wherein prior to, during, or after proliferating the T cells, the T cells are mixed with a vector having a nucleic acid sequence encoding a chimeric antigen receptor, wherein the chimeric antigen receptor comprises cancer targeting sequence, a transmembrane domain, a T cell costimulatory molecule domain, and a signal-transduction component of a T-cell antigen receptor domain under conditions such that the cells express a chimeric antigen receptor on the surface of the cells.

In certain embodiments, the disclosure relates to in vitro cell culture compositions comprising a minimal essential medium and T cells and a peptide disclosed herein or nanoparticle comprising a peptide disclosed herein and a phosphatidylinositol-3-kinase inhibitor, VIP-degrading enzyme, and combinations thereof and optionally further comprising anti-CD3 antibodies and anti-CD28 antibodies optionally immobilized on a solid substrate such as beads. In certain embodiments, the T cells are purified from bone marrow cells or blood cells, peripheral blood.

In certain embodiments, the phosphatidylinositol-3-kinase inhibitor is selected from idelalisib, wortmannin, demethoxyviridin, perifosine, buparlisib, duvelisib, copanlisib, and alpelisib. In certain embodiments, the phosphatidylinositol-3-kinase inhibitor is selected from idelalisib in a culture at a concentration of greater than 0.001, 0.1, 1, 10, 100 nM or between 10 nM and 10 micromolar or between 10 nM and 500 nM, or between 10 nM and 1 micromolar.

In certain embodiments, the culture comprises an enzyme that hydrolyses VIP. In certain embodiments, the culture comprises a VIP degrading enzyme such as a peptidase, serine peptidase, a tryptase, chymase, or human chymase 1 (CMA1). In certain embodiments, the culture has at least at least 0.001, 0.01, 0.1, or 1 microgram per mL of the VIP degrading enzyme such as a mast cell chymase. In certain embodiments, the disclosure contemplates a T cells culture comprising a minimal essential medium and isolated cells that express CD3 and/or CD4 and/or CD8 and are negative for CD27 and/or CD28 and a PI3 kinase inhibitor, a peptide disclosed herein or a nanoparticle comprising a peptide disclosed herein, and combinations thereof. The cells may be isolated by negative or positive selection using binding agents attached to solid supports such as beads, magnetic beads, or particles of fluorescent binding agents.

In certain embodiments, the anti-CD3 antibodies and anti-CD28 antibodies are immobilized on a bead, magnetic bead, or solid surface. In certain embodiments, more than 5.0% or 10% or 15% of the total cells in the culture express CD3 and/or CD4 and/or CD8. In certain embodiments, more than 20%, 25% or 50% of the total cells express CD3 and/or CD4 and/or CD8. In certain embodiments, more than 15% or 20% or 30% of the T cells in the culture are negative for CD28 and/or CD27. In certain embodiments, more than 20%, 25% or 50% of the T cells are negative for CD28 and/or CD27.

In certain embodiments, the purified T cells are obtained from centrifuging blood under conditions such that plasma and red blood cells separate providing purified T cells in a mixture of white blood cells between the plasma and red blood cells. In certain embodiments, the purified T cells are obtained by bone marrow aspirates or a bone marrow biopsy.

In certain embodiments, the purified T cells are obtained by mixing cells with a fluorescent marker that binds CD3 and purifying cells by fluorescent activated cell sorting. In certain embodiments, the purified T cells are obtained by mixing cells with a magnetized marker that binds CD3 and purifying cells by magnetic sorting. In certain embodiments, the purified T cells are obtained by mixing cells with a fluorescent marker that binds CD3 and/or CD4 and/or CD8 and purifying cells by fluorescent activated cell sorting. In certain embodiments, the purified T cells are obtained by mixing cells with a magnetized marker that binds CD3 and/or CD4 and/or CD8 and purifying cells by magnetic sorting.

In certain embodiments, the disclosure contemplates a solid substrate, such as beads, with anti-CD3 and anti-CD28 antibodies and having a VIP-degrading enzyme coupled to the surface. In certain embodiments, it is contemplated that the beads are arranged in the medium and the T cells are expanded on top of the medium such that the beads are sub-cellular.

In certain embodiments, the VIP degrading enzyme comprises human CMA1 Accession number GenBank: AAI03975.1:

```
                                           (SEQ ID NO: 13)
MLLKLKEKASLTLAVGTLPFPSQFNFVPPGRMCRVAGWGRTGVLKPGSD
TLQEVKLRLMDPQACSHFRDFDHNLQLCVGNPRKTKSAFKGDSGGPLLC
AGVAQGIVSYGRSDAKPPAVFTRISHYRPWINQILQAN.
```

In certain embodiments, the VIP-degrading enzyme is human recombinant enkephalinase (neutral endopeptidase, EC 3.4.24.11) having (SEQ ID NO: 14):

```
DGICKSSDCIKSAARLIQNMDATTEPCTDFFKYACGGWLKRNVIPETSS

RYGNFDILRDELEVVLKDVLQEPKTEDIVAVQKAKALYRSCINESAIDS

RGGEPLLKLLPDIYGWPVATENWEQKYGASWTAEKAIAQLNSKYGKKVL

INLFVGTDDKNSVNHVIHIDQPRLGLPSRDYYECTGIYKEACTAYVDFM

ISVARLIRQEERLPIDENQLALEMNKVMELEKEIANATAKPEDRNDPML

LYNKMTLAQIQNNFSLEINGKPFSWLNFTNEIMSTVNISITNEEDVVVY

APEYLTKLKPILTKYSARDLQNLMSWRFIMDLVSSLSRTYKESRNAFRK

ALYGTTSETATWRRCANYVNGNMENAVGRLYVEAAFAGESKHVVEDLIA

QIREVFIQTLDDLTWMDAETKKRAEEKALAIKERIGYPDDIVSNDNKLN

NEYLELNYKEDEYFENIIQNLKFSQSKQLKKLREKVDKDEWISGAAVVN

AFYSSGRNQIVFPAGILQPPFFSAQQSNSLNYGGIGMVIGHEITHGFDD

NGRNFNKDGDLVDWWTQQSASNFKEQSQCMVYQYGNFSWDLAGGQHLNG

INTLGENIADNGGLGQAYRAYQNYIKKNGEEKLLPGLDLNHKQLFFLNF

AQVWCGTYRPEYAVNSIKTDVESPGNFRIIGTLQNSAEFSEAFHCRKNS

YMNPEKKCRVW.
```

In certain embodiments, cell cultures and methods described herein further include IL-12. In certain embodiments, the IL-12 is contemplated to enhance the effect of peptide disclosed herein or nanoparticle thereof on T cell proliferation stimulated in vitro with antibodies to CD3 and CD28.

In certain embodiments, the disclosure relates to expanding T cells, or expanding or reversing senescence in T cells, with a naturally occurring reactivity to cancer can be found infiltrated in tumors of the subject. The tumor can be harvested, and these tumor-infiltrating lymphocytes (TIL) can be expanded using methods discloses herein.

Some cancers are caused by viruses, and traditional vaccines against those viruses, such as HPV vaccine and Hepatitis B vaccine, will prevent those cancers. It is contemplated that peptide disclosed herein can be administered in combination with these vaccines to improve treatment efficacy.

It is believed that cancer cells arise and are destroyed by the immune system, and that cancer forms when the immune system fails to destroy them. One approach to cancer vaccination is to separate proteins from cancer cells and immunize cancer patients against those proteins, stimulating an immune reaction that kills the cancer cells. Cancer vaccines are contemplated for the treatment of breast, lung, colon, skin, kidney, prostate, and other cancers. In certain embodiments, the disclosure relates to treating cancers by administering a peptide disclosed herein in combination with cancer antigens.

In certain embodiments, the disclosure relates to methods of treating or preventing a viral infection comprising administering a peptide disclosed herein to a subject at risk of, exhibiting symptoms of, or diagnosed with a viral infection. In certain embodiments, the subject is immune compromised or the subject is an allogeneic bone marrow transplant donor or recipient. In typical embodiments, the subject is an organ transplant recipient, undergoing hemodialysis, diagnosed with cancer, receiving an immunosuppressive drug, and/or diagnosed with an HIV-infection. In certain embodiments, the disclosure relates to preventing a viral infection in an immunocompromised subject at risk of infection by administering a peptide disclosed herein and optionally one or more antiviral agents.

In some embodiments, the disclosure relates to the use of a peptide disclosed herein in the production of an anti-viral medicament for the treatment of a viral infection. In some embodiments, the subject is diagnosed with a chronic viral infection. In certain embodiments, the subject undergoes serological monitoring. In some embodiments, the administration is under conditions such that the viral infection is no longer detected. In some embodiments, the subject is diagnosed with a RNA virus, DNA virus, or retroviruses. In some embodiments, the subject is diagnosed with a virus that is double stranded DNA virus, sense single stranded DNA virus, double stranded RNA virus, sense single stranded RNA virus, antisense single stranded RNA virus, sense single stranded RNA retrovirus or a double stranded DNA retrovirus. In some embodiments, the subject is diagnosed to have a rotavirus, an influenza virus, a herpes virus, a hepatitis virus, or a lentivirus. In some embodiments, titer of the virus in the subject is reduced after the treatment as compared to pre-treatment.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In some embodiments, the disclosure relates to treating or preventing a viral infection by administering a peptide disclosed herein in combination with a second antiviral agent. In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fosamprenavir, foscarnet, ganciclovir, idoxuridine, imiquimod, indinavir, inosine, interferon type III, interferon type II, interferon type I, lamivudine, lopinavir, maraviroc, moroxydine, methisazone, nelfinavir, nevirapine, oseltamivir (Tamiflu), peginterferon alfa-2a, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, Truvada™ (emtricitabine/tenofovir disoproxil fumarate), valacyclovir, valaciclovir, vicriviroc, vidarabine, viramidine, zalcitabine, zanamivir, and/or zidovudine. In certain embodiments, the subject is administered a pharmaceutical composition comprising a peptide disclosed herein and a second antiviral agent.

In certain embodiments, the disclosure relates to treating a subject with a viral infection after infection by administering a peptide disclosed herein and an immunoglobulin.

In certain embodiments, the disclosure relates to treating or preventing a viral infection by administering a peptide disclosed herein and a viral vaccine or in the absence of a viral vaccine.

In certain embodiments, the disclosure relates to enhancing the immune response to a vaccine comprising administering a peptide disclosed herein to a subject in need thereof. Typically, the vaccine is selected from the group of vaccines consisting of herpes zoster vaccine, smallpox vaccine, polio vaccine, pertussis vaccine, influenza vaccine, diphtheria vaccine, tetanus vaccine, meningococcal vaccine, influenza A vaccine including subtype H1N1 vaccine, influenza B vaccine, influenza C vaccine, rotavirus A vaccine, rotavirus B vaccine, rotavirus C vaccine, rotavirus D vaccine, rotavirus E vaccine, SARS coronavirus vaccine, human adenovirus types (HAdV-1 to 55) vaccine, human papillomavirus (HPV) vaccine, parvovirus B19 vaccine, molluscum contagiosum vaccine, JC vaccine, BK vaccine, Merkel cell polyomavirus vaccine, coxsackie A vaccine, norovirus vaccine, Rubella vaccine, lymphocytic choriomeningitis vaccine, yellow fever vaccine, measles vaccine, mumps vaccine, respiratory syncytial vaccine, rinderpest vaccine, California encephalitis vaccine, hantavirus vaccine, rabies vaccine, ebola vaccine, marburg vaccine, herpes simplex virus-1 (HSV-1) vaccine, herpes simplex virus-2 (HSV-2) vaccine, varicella zoster vaccine, Epstein-Barr virus (EBV) vaccine, cytomegalovirus (CMV) vaccine, herpes lymphotropic vaccine, roseolovirus vaccine, Kaposi's sarcoma-associated herpesvirus vaccine, hepatitis A (HAV) vaccine, hepatitis B (HBV) vaccine, hepatitis C (HCV) vaccine, hepatitis D (HDV) vaccine, hepatitis E (HEV) vaccine, human immunodeficiency virus (HIV) vaccine, The Human T-lymphotropic virus Type I (HTLV-1) vaccine, Friend spleen focus-forming virus (SFFV) vaccine, and Xenotropic MuLV-Related Virus (XMRV) vaccine. In certain embodiments, the vaccine for a subject diagnosed with a chronic viral infection.

In certain embodiments, the vaccine comprises a protein or peptide, carbohydrate, sugar, polysaccharide, or nucleic acid. Typically, the vaccine is an attenuated replication competent virus or an inactivated virus. In certain embodiments, the vaccine comprises a live or a killed or inactivated prokaryotic or eukaryotic cell.

In certain embodiments, the human T cells are activated in vitro by co-incubation with viral antigens. In certain embodiments, the viral antigens are presented on microvesicles. In certain embodiments, the viral antigens are presented on dendritic cells.

Nucleic acid vaccines, typically a DNA plasmid, are genetically engineered to encode and/or produce one or more antigens from a pathogen. The nucleic acid transfects or infects host cells, where the inner machinery of the cells expresses the proteins. Because these proteins are recognized as foreign, when they are processed by the host cells and displayed on their surface immune response is triggered. Cytotoxic T lymphocytes responses can also be enhanced by co-inoculation with co-stimulatory molecules such as GM-CSF, B7-1, or B7-2. In certain embodiments, a peptide disclosed herein may be administered in combination with nucleic acid vaccines or other co-stimulatory molecules.

In certain embodiments, the disclosure relates to vaccine compositions comprising a peptide disclosed herein and methods of administering a peptide disclosed herein in combination with a vaccine. In certain embodiments, the vaccine contains an antigen from a pathogen and is presented to the immune system from weakened or killed forms of the microbe or its toxins. The antigen stimulates the immune system. Vaccines may be prophylactic (e.g. to prevent or ameliorate the effects of a future infection by any pathogen), or therapeutic by being administered after infection or diagnosis of the disease.

Some vaccines contain killed, but previously virulent, microorganisms that have been destroyed with chemicals or heat. The influenza vaccine, cholera vaccine, bubonic plague vaccine, polio vaccine, hepatitis A vaccine, and rabies vaccine are examples of a killed vaccine that are contemplated by this disclosure.

Some vaccines contain live, attenuated microorganisms. Typically, these are live viruses that have been cultivated under conditions that disable certain virulent properties, or which use closely related but less dangerous organisms to produce a broad immune response; however, some are bacterial in nature.

In certain embodiments, the vaccine is a protein subunit. Rather than introducing an inactivated or attenuated microorganism to an immune system, a fragment of it can be used to create an immune response. Examples include the subunit vaccine against Hepatitis B virus that is composed of only the surface proteins of the virus, the virus-like particle (VLP) vaccine against human papillomavirus (HPV) that is composed of the viral major capsid protein, and the hemagglutinin and neuraminidase subunits of the influenza virus.

In certain embodiments, the vaccine comprises a polysaccharide. Certain bacteria have polysaccharide outer coats that are typically immunogenic. By linking these polysaccharides to proteins (e.g. toxins), the immune system can be led to recognize the polysaccharide as if it were a protein antigen.

Toxoid vaccines are made from inactivated toxic compounds. Examples of toxoid-based vaccines include diphtheria and tetanus toxoid. In certain embodiments, a peptide disclosed herein is administered in combination with DPT. DPT (also DTP and DTwP) refers to a class of combination vaccines against three infectious diseases in humans: diphtheria, pertussis (whooping cough) and tetanus. The vaccine components include diphtheria and tetanus toxoids, and killed whole cells of the organism that causes pertussis (wP). DTaP (also known as Tdap, DTPa, and TDaP) refers to similar combination vaccines in which the pertussis component is acellular. Also contemplated is the DT or TD vaccine, which lacks the pertussis component.

Other specific vaccines contemplated by the disclosure include the anthrax vaccine, e.g., culture filtrates of an avirulent, nonencapsulated strain known as V770-NP1-R, Bacille Calmette-Guerin (BCG), e.g., a strain of the attenuated live bovine tuberculosis *bacillus, Haemophilus influenzae* type B vaccine, e.g., Hib polysaccharide-protein conjugate vaccine, hepatitis A vaccine, e.g., inactivated Hepatitis A virus, hepatitis B vaccine, e.g., hepatitis B surface antigen, human papillomavirus (HPV) vaccine, e.g., non-infectious virus-like particles assembled from the L1 proteins of HPV types 6, 11, 16 and 18, meningococcal vaccine, e.g., capsular polysaccharide antigens of *Neisseria meningitides* serogroups A, C, Y, and W-135 strains individually conjugated to diphtheria toxoid protein.

In certain embodiments, this disclosure relates to methods of treating an active cytomegalovirus infection comprising administering an effective amount of a vasoactive intestinal peptide antagonist disclosed herein to a subject diagnosed with and exhibiting signs or symptoms of an active cytomegalovirus infection, wherein the vasoactive intestinal peptide antagonist comprises a peptide having a C-terminal amide and is optionally modified with hydrocarbon or polyethylene glycol groups.

In certain embodiments, the subject has a compromised immune system. In certain embodiments, the subject is a transplant recipient.

In certain embodiments, this disclosure relates to methods of reducing an active cytomegalovirus infection comprising administering an effective amount of a vasoactive intestinal peptide antagonist disclosed herein to a subject suffering from an active cytomegalovirus infection, wherein the vasoactive intestinal peptide antagonist comprises a peptide having a C-terminal amide and is optionally modified with hydrocarbon or polyethylene glycol groups. In certain embodiments, a titer of cytomegalovirus in the subject is reduced after administering the vasoactive intestinal peptide antagonist as compared to pretreatment.

EXAMPLES

Improved VIP Antagonists

Whether tumor specific expression of vasoactive intestinal polypeptide represents a mechanism of tumor-mediated immune escape was evaluated. There is a spectrum of VIP expression across tumors with highest expression being seen in pancreatic exocrine cancer and lowest expression seen in melanoma. In general, levels of VIP expression by tumors are inversely proportional to the expression of other co-inhibitory pathway molecules such as PDL1. Tumors expressing and secreting VIP may have mutations in VIP coding sequence, such that the resultant peptide molecule has improved pharmacokinetics or pharmacodynamics in the tumor microenvironment. A pharmacokinetic advantage might be the consequence of a mutation that reduces VIP less susceptible to proteases, improving its half-life. A pharmacodynamic advantage might be the consequence of a mutation that enhances binding affinity to the receptor, thus enhancing signaling.

Figure 3:
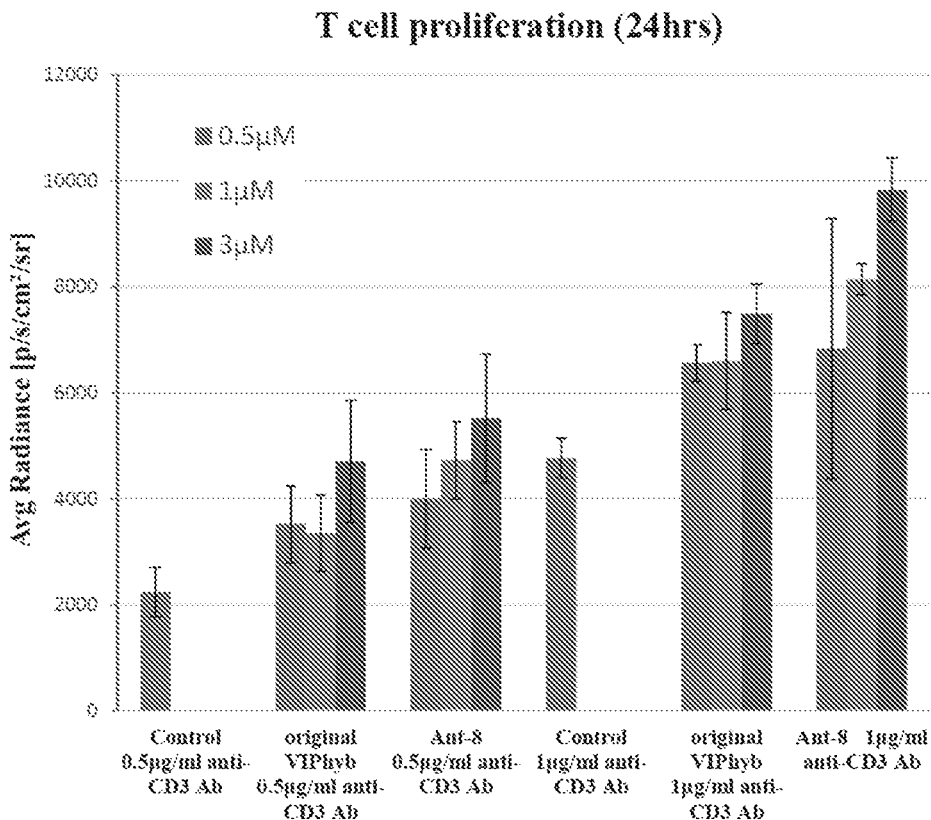
FIG. 3 shows data on T cell proliferation at 24 hr in the presence of the original VIPhyb and Ant-8. T cells from luciferase+C57/BL6 mice were harvested and cultured in 96-well plate with either 0.5 µg/ml or 1 µg/ml anti-CD3 antibody and 30 U/ml IL-2 in the presence of original VIPhyb or Ant-8 at 0.5 µM, 1 µM or 3 µM.
Figure 4:
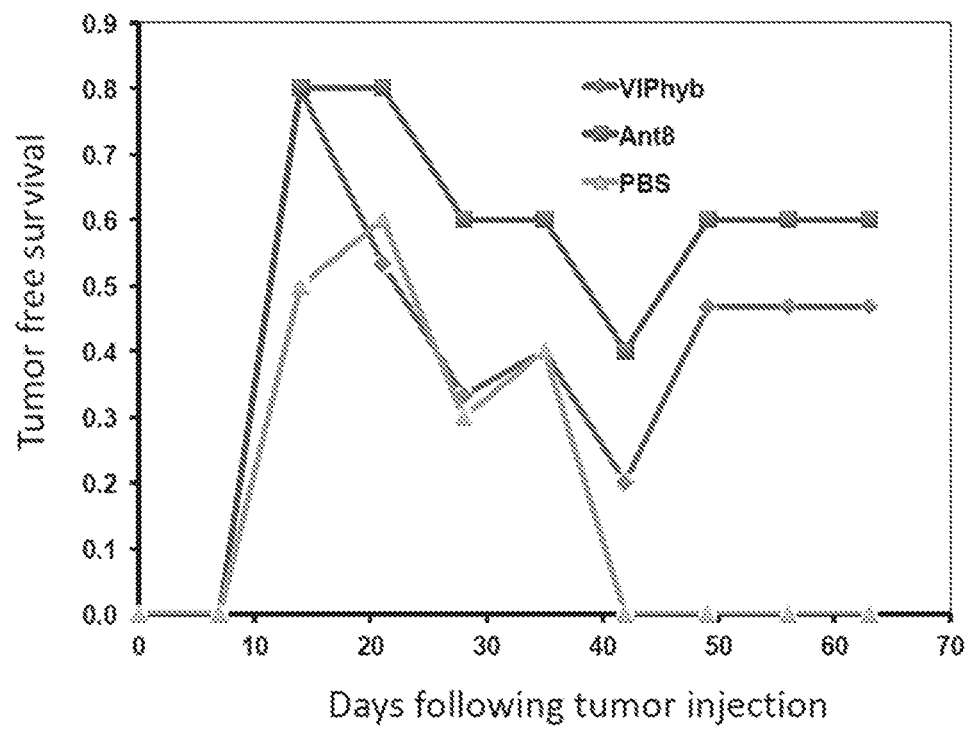
FIG. 4 shows data where VIPhyb, Ant8, or PBS were subcutaneously injected daily to mice for 7 days from the day following inoculation of leukemia cells intravenously.
Figure 5:
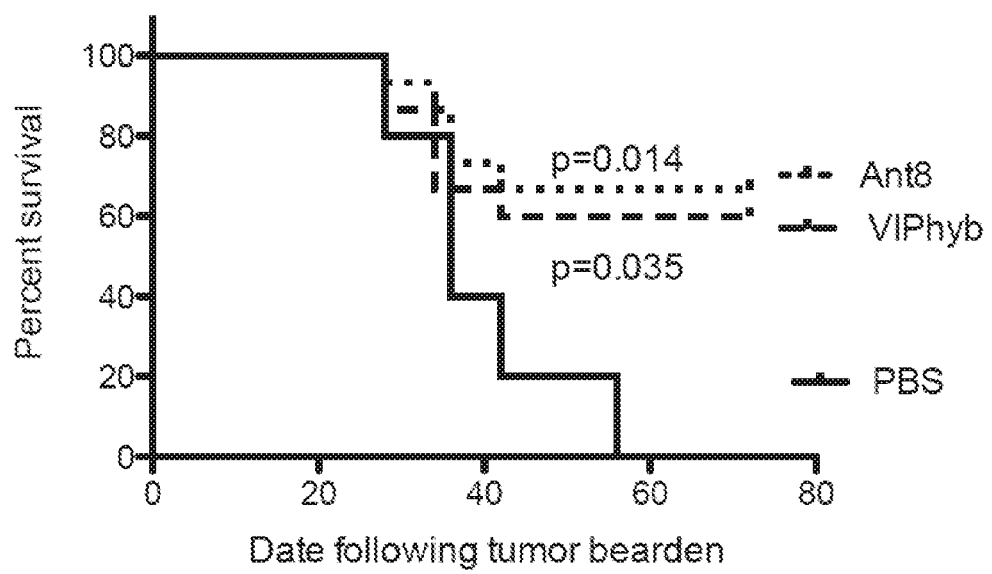
FIG. 5 shows survival data in leukemia-bearing mice (C1498) treated with ANT-8.
Figure 6A:
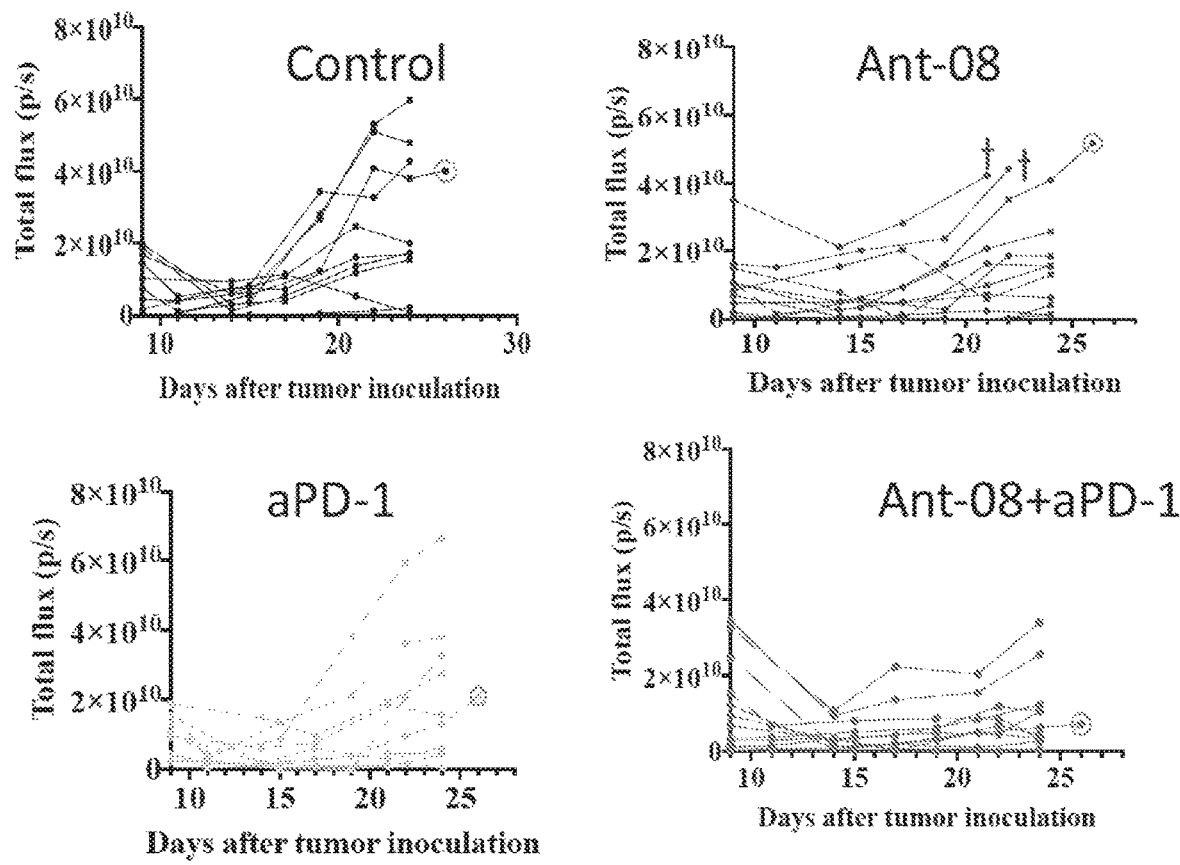
FIG. 6A shows data using KPC luc, a murine luciferase transfected pancreatic cancer cell line injected in the tail of the pancreas of immunocompetent mice that were treated with Ant-08 and/or anti-PD1. Slower tumor growth rate was observed in Ant-08+anti-PD1 treated mice.
Figure 6B:
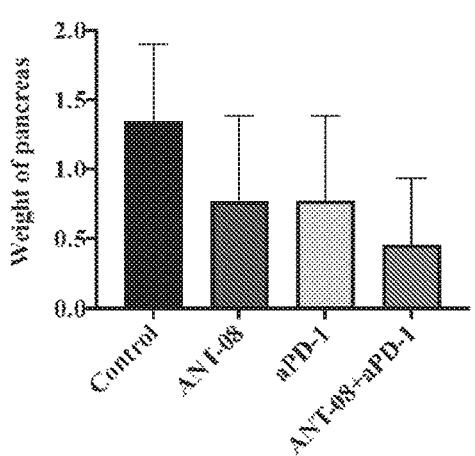
FIG. 6B shows data on tumor burden in an orthotopic KPC model. Pancreas isolated from above mice at the time of sacrifice (day 24) were weighed for tumor burden. Significantly small tumor burden was observed in Ant-08+anti-PD1 treated mice.
Figure 6C:
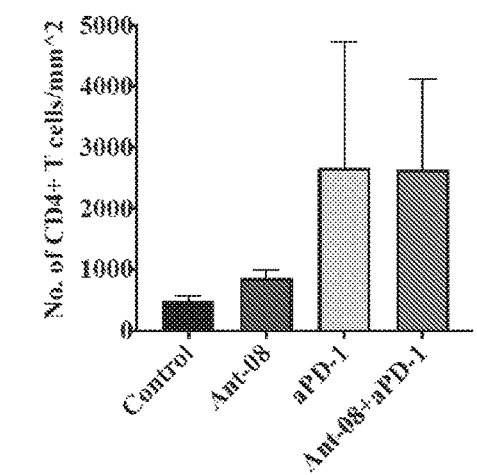
FIG. 6C shows data on CD+4 T cell infiltration in the orthotopic KPC model. Increased infiltration of CD4 T cells were observed in the tumors of mice treated with Ant-08+ anti-PD1.
Figure 6D:
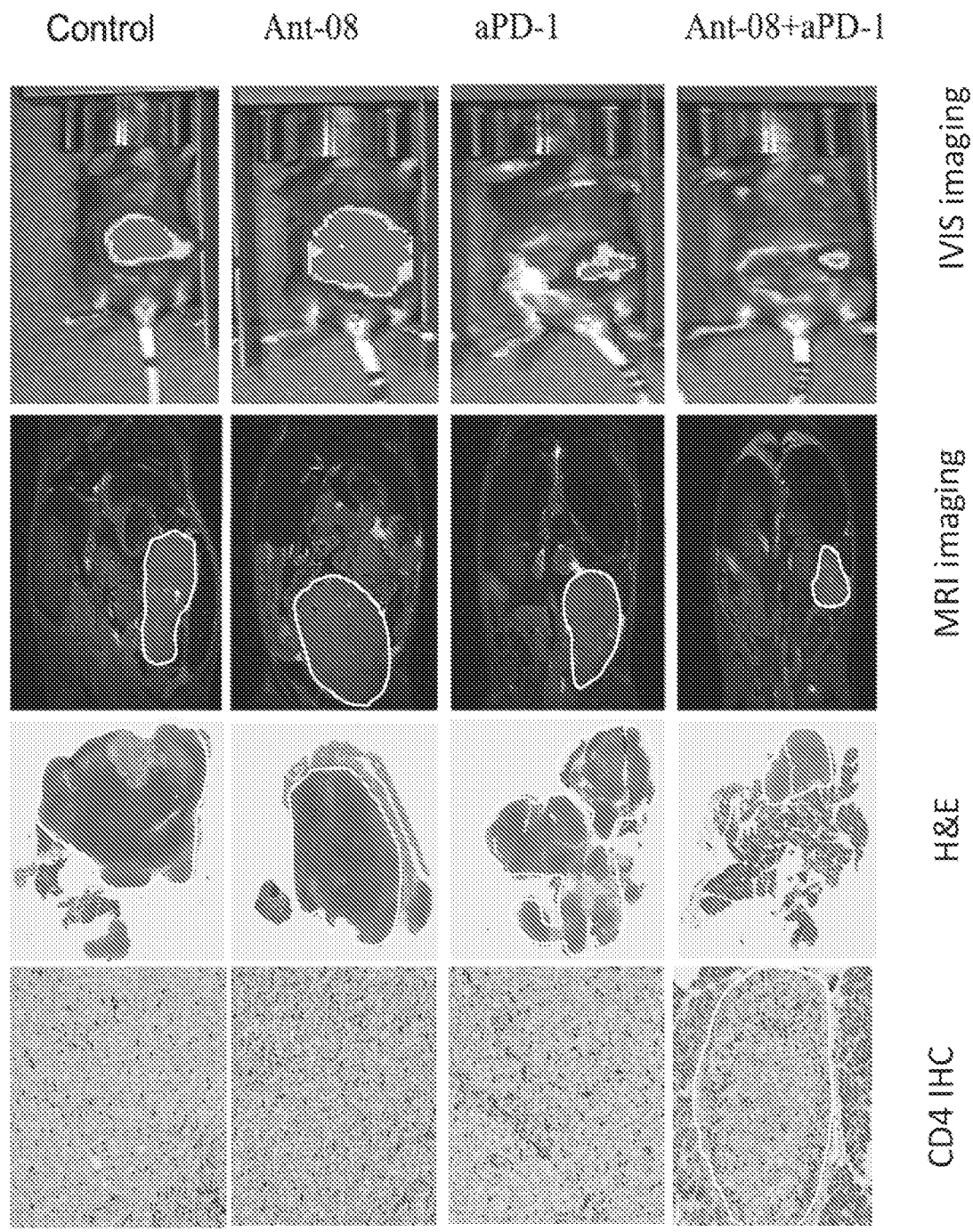
FIG. 6D shows IVIS and MM imaging of Mice at day 26. The tumors from these mice were stained via H&E and CD4.
Figure 7:
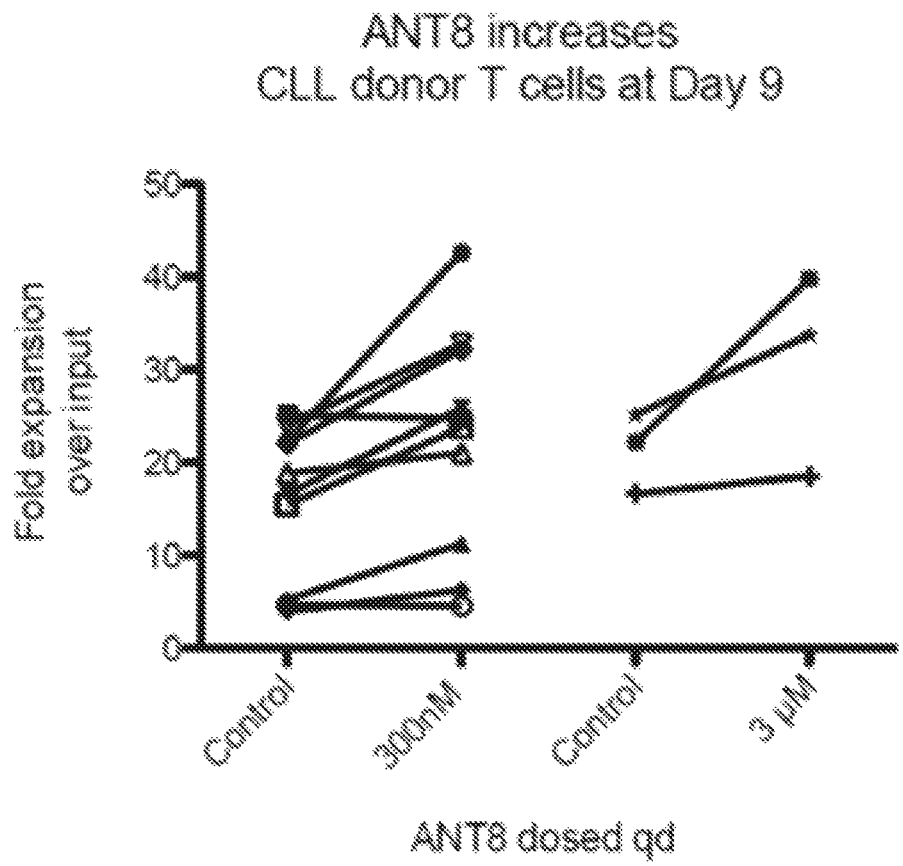
FIG. 7 shows data using ANT8 indicating enhance yields of T cells from Chronic lymphocytic leukemia (CLL) donors during ex vivo expansion with anti-CD3/28 beads and 30 U/mL IL-2.

Experiments were performed to determine whether mutated VIP produced by tumors would lead to more sustained suppression of anticancer T-cells in the tumor microenvironment. Analyzing mutations in specific genes curated from deposited tumor sequences, there are multiple cancers with mutations in the coding sequence of VIP. In particular, there were 140 missense mutations and 17 truncating mutations within the VIP gene cluster listed in the Cancer Genome Atlas. Within the coding sequence of the 28 amino acid VIP peptide, mutations were identified in VIP coding sequence present in breast cancer, prostate adenocarcinoma, esophageal adenocarcinoma, cutaneous melanoma, small-cell lung cancer, stomach adenocarcinoma, uterine endometrial carcinoma, cutaneous melanoma, esophageal adenocarcinoma, colorectal adenocarcinoma, uterine carcinosarcoma, hepatocellular adenoma, lung adenocarcinoma, stomach adenocarcinoma. Eight specific mutations that were present in the C-terminal amino acids including the alpha helix of VIP that binds the receptor.

The alpha helix sequence is common between VIP, the peptide agonist, which is immunosuppressive. VIPhyb (SEQ ID NO: 1), the antagonistic peptide that differs in the six internal amino acids from native VIP (SEQ ID NO: 2) (See FIG. 1). The eight sequences, ANT-1 through 8, were prepared with the presence of the six N-terminal amino acids of VIPhyb (See SEQ ID NO: 3-10 in FIG. 1.) In particular, the ANT-1 sequences has an amino acid T to A substitution at amino acid position seven. The ANT-2 sequence has an amino substitution of D to V at amino acid position number 8. The ANT-3 had an amino acid substitution of Y to C at amino acid position number 10. The ANT-4 has an amino acid substitution R to S at amino acid position 12. The ANT-5 has an amino acid substitution M to I at amino acid position number 17. The ANT-6 has an amino acid substitution K to N at amino acid position 20. The ANT-7 has an amino acid substitution L to M at amino acid position number 23. The ANT-8 has an amino acid substitution S to L at amino acid position number 25. Each of the alternative antagonistic peptide sequence ANT-1 through ANT-8 was synthesized.

The peptides (SEQ ID NO: 3-10 in FIG. 1) were added to short-term cultures of luciferase positive T-cells cultured in the presence of plate bound anti CD3 antibody in 96 well plates. The concentration of anti-CD3 antibody was either 0.5 mcg per ml or 1 mcg per ml. The T-cells from luciferase transgenic mice were added in the presence of low-dose IL-2 and 0.5 micromolar, 1 micromolar, or 3 micromolar concentrations of the original VIPhyb peptide or the alternative ANT-1 to ANT-8 peptide sequences were added. FIG. 2 shows T cell proliferation at 24 hours in the presence of Ant-1 through Ant-8 at 1 micromolar concentration. FIG. 3 shows enhanced T-cell proliferation at 24 hours in the presence of the ANT-8 peptide at 0.5 micromolar, 1 micromolar and 3 micromolar concentrations compared to the original VIPhyb peptide at the same corresponding concentrations.

The enhanced T-cell proliferation using lower concentrations of anti-CD3 with the ANT-8 peptide were more modest and not significantly different from control cultures that contained and only marginally increased compared to control cultures containing plate bound anti-CD3 antibody with no added peptides. A unique peptide sequences with improved antagonist activity compared to the native VIPhyb was identified, ANT-8 (SEQ ID NO: 10).

The invention claimed is:

1. A peptide comprising the amino acid sequence KPRRPYTDNYTRLRKQMAVKKYLNLILN (SEQ ID NO: 10).

2. The peptide of claim 1, wherein the peptide is conjugated to a nanoparticle.

3. A pharmaceutical composition comprising the peptide of claim 1 and a pharmaceutically acceptable excipient.

4. The pharmaceutical composition of claim 3 in the form of a capsule, tablets, pill, powder, or granule.

5. The pharmaceutical composition of claim 3 in the form of a sterilized pH buffered aqueous salt solution.

6. The pharmaceutical composition of claim 3 in a container configured to spray a liquid or sealed container with a propellant.

* * * * *

SEQUENCE LISTING

```
<160> NUMBER OF SEQ ID NOS: 15

<210> SEQ ID NO 1
<211> LENGTH: 28
<212> TYPE: PRT
<213> ORGANISM: Artificial
<220> FEATURE:
<223> OTHER INFORMATION: Synthetic construct

<400> SEQUENCE: 1

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 28
<212> TYPE: PRT
<213> ORGANISM: Artificial
<220> FEATURE:
<223> OTHER INFORMATION: Synthetic construct

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 28
<212> TYPE: PRT
<213> ORGANISM: Artificial
<220> FEATURE:
<223> OTHER INFORMATION: Synthetic construct

<400> SEQUENCE: 3

Lys Pro Arg Arg Pro Tyr Ala Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 28
<212> TYPE: PRT
<213> ORGANISM: Artificial
<220> FEATURE:
<223> OTHER INFORMATION: Synthetic construct

<400> SEQUENCE: 4

Lys Pro Arg Arg Pro Tyr Thr Val Asn Tyr Thr Arg Leu Arg Lys Gln
1               5                   10                  15

Met Ala Val Lys Lys Tyr Leu Asn Ser Ile Leu Asn
            20                  25
```

```
<210> SEQ ID NO 5
<211> LENGTH: 28
<212> TYPE: PRT
<213> ORGANISM: Artificial
<220> FEATURE:
<223> OTHER INFORMATION: Synthetic construct

<400> SEQUENCE: 5

Lys Pro Arg Arg Pro Tyr Thr Asp Asn Cys Thr Arg Leu Arg Lys Gln
1               5                   10                  15

Met Ala Val Lys Lys Tyr Leu Asn Ser Ile Leu Asn
            20                  25

<210> SEQ ID NO 6
<211> LENGTH: 28
<212> TYPE: PRT
<213> ORGANISM: Artificial
<220> FEATURE:
<223> OTHER INFORMATION: Synthetic construct

<400> SEQUENCE: 6

Lys Pro Arg Arg Pro Tyr Thr Asp Asn Tyr Thr Ser Leu Arg Lys Gln
1               5                   10                  15

Met Ala Val Lys Lys Tyr Leu Asn Ser Ile Leu Asn
            20                  25

<210> SEQ ID NO 7
<211> LENGTH: 28
<212> TYPE: PRT
<213> ORGANISM: Artificial
<220> FEATURE:
<223> OTHER INFORMATION: Synthetic construct

<400> SEQUENCE: 7

Lys Pro Arg Arg Pro Tyr Thr Asp Asn Tyr Thr Arg Leu Arg Lys Gln
1               5                   10                  15

Ile Ala Val Lys Lys Tyr Leu Asn Ser Ile Leu Asn
            20                  25

<210> SEQ ID NO 8
<211> LENGTH: 28
<212> TYPE: PRT
<213> ORGANISM: Artificial
<220> FEATURE:
<223> OTHER INFORMATION: Synthetic construct

<400> SEQUENCE: 8

Lys Pro Arg Arg Pro Tyr Thr Asp Asn Tyr Thr Arg Leu Arg Lys Gln
1               5                   10                  15

Met Ala Val Asn Lys Tyr Leu Asn Ser Ile Leu Asn
            20                  25

<210> SEQ ID NO 9
<211> LENGTH: 28
<212> TYPE: PRT
<213> ORGANISM: Artificial
<220> FEATURE:
<223> OTHER INFORMATION: Synthetic construct

<400> SEQUENCE: 9

Lys Pro Arg Arg Pro Tyr Thr Asp Asn Tyr Thr Arg Leu Arg Lys Gln
1               5                   10                  15

Met Ala Val Lys Lys Tyr Met Asn Ser Ile Leu Asn
            20                  25
```

<210> SEQ ID NO 10
<211> LENGTH: 28
<212> TYPE: PRT
<213> ORGANISM: Artificial
<220> FEATURE:
<223> OTHER INFORMATION: Synthetic construct

<400> SEQUENCE: 10

Lys Pro Arg Arg Pro Tyr Thr Asp Asn Tyr Thr Arg Leu Arg Lys Gln
1               5                   10                  15

Met Ala Val Lys Lys Tyr Leu Asn Leu Ile Leu Asn
            20                  25

<210> SEQ ID NO 11
<211> LENGTH: 28
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(28)
<223> OTHER INFORMATION: X is any amino acid

<400> SEQUENCE: 11

Lys Pro Arg Arg Pro Tyr Xaa Xaa Asn Xaa Thr Xaa Leu Arg Lys Gln
1               5                   10                  15

Xaa Ala Val Xaa Lys Tyr Xaa Asn Xaa Ile Leu Asn
            20                  25

<210> SEQ ID NO 12
<211> LENGTH: 34
<212> TYPE: PRT
<213> ORGANISM: Artificial
<220> FEATURE:
<223> OTHER INFORMATION: Synthetic construct

<400> SEQUENCE: 12

Lys Pro Arg Arg Pro Tyr Thr Asp Asn Tyr Thr Arg Leu Arg Lys Gln
1               5                   10                  15

Met Ala Val Lys Lys Tyr Leu Asn Leu Ile Leu Asn Gly Gly Gly Gly
            20                  25                  30

Ser Cys

<210> SEQ ID NO 13
<211> LENGTH: 136
<212> TYPE: PRT
<213> ORGANISM: Homo sapiens

<400> SEQUENCE: 13

Met Leu Leu Lys Leu Lys Glu Lys Ala Ser Leu Thr Leu Ala Val Gly
1               5                   10                  15

Thr Leu Pro Phe Pro Ser Gln Phe Asn Phe Val Pro Pro Gly Arg Met
            20                  25                  30

Cys Arg Val Ala Gly Trp Gly Arg Thr Gly Val Leu Lys Pro Gly Ser
            35                  40                  45

Asp Thr Leu Gln Glu Val Lys Leu Arg Leu Met Asp Pro Gln Ala Cys
        50                  55                  60

Ser His Phe Arg Asp Phe Asp His Asn Leu Gln Leu Cys Val Gly Asn
65                  70                  75                  80

Pro Arg Lys Thr Lys Ser Ala Phe Lys Gly Asp Ser Gly Gly Pro Leu
                85                  90                  95

```
Leu Cys Ala Gly Val Ala Gln Gly Ile Val Ser Tyr Gly Arg Ser Asp
                100                 105                 110

Ala Lys Pro Ala Val Phe Thr Arg Ile Ser His Tyr Arg Pro Trp
        115                 120                 125

Ile Asn Gln Ile Leu Gln Ala Asn
    130                 135

<210> SEQ ID NO 14
<211> LENGTH: 697
<212> TYPE: PRT
<213> ORGANISM: Homo sapiens

<400> SEQUENCE: 14

Asp Gly Ile Cys Lys Ser Ser Asp Cys Ile Lys Ser Ala Ala Arg Leu
1               5                   10                  15

Ile Gln Asn Met Asp Ala Thr Thr Glu Pro Cys Thr Asp Phe Phe Lys
            20                  25                  30

Tyr Ala Cys Gly Gly Trp Leu Lys Arg Asn Val Ile Pro Glu Thr Ser
        35                  40                  45

Ser Arg Tyr Gly Asn Phe Asp Ile Leu Arg Asp Glu Leu Glu Val Val
    50                  55                  60

Leu Lys Asp Val Leu Gln Glu Pro Lys Thr Glu Asp Ile Val Ala Val
65                  70                  75                  80

Gln Lys Ala Lys Ala Leu Tyr Arg Ser Cys Ile Asn Glu Ser Ala Ile
                85                  90                  95

Asp Ser Arg Gly Gly Glu Pro Leu Leu Lys Leu Leu Pro Asp Ile Tyr
            100                 105                 110

Gly Trp Pro Val Ala Thr Glu Asn Trp Glu Gln Lys Tyr Gly Ala Ser
        115                 120                 125

Trp Thr Ala Glu Lys Ala Ile Ala Gln Leu Asn Ser Lys Tyr Gly Lys
    130                 135                 140

Lys Val Leu Ile Asn Leu Phe Val Gly Thr Asp Asp Lys Asn Ser Val
145                 150                 155                 160

Asn His Val Ile His Ile Asp Gln Pro Arg Leu Gly Leu Pro Ser Arg
                165                 170                 175

Asp Tyr Tyr Glu Cys Thr Gly Ile Tyr Lys Glu Ala Cys Thr Ala Tyr
            180                 185                 190

Val Asp Phe Met Ile Ser Val Ala Arg Leu Ile Arg Gln Glu Glu Arg
        195                 200                 205

Leu Pro Ile Asp Glu Asn Gln Leu Ala Leu Glu Met Asn Lys Val Met
    210                 215                 220

Glu Leu Glu Lys Glu Ile Ala Asn Ala Thr Ala Lys Pro Glu Asp Arg
225                 230                 235                 240

Asn Asp Pro Met Leu Leu Tyr Asn Lys Met Thr Leu Ala Gln Ile Gln
                245                 250                 255

Asn Asn Phe Ser Leu Glu Ile Asn Gly Lys Pro Phe Ser Trp Leu Asn
            260                 265                 270

Phe Thr Asn Glu Ile Met Ser Thr Val Asn Ile Ser Ile Thr Asn Glu
        275                 280                 285

Glu Asp Val Val Val Tyr Ala Pro Glu Tyr Leu Thr Lys Leu Lys Pro
    290                 295                 300

Ile Leu Thr Lys Tyr Ser Ala Arg Asp Leu Gln Asn Leu Met Ser Trp
305                 310                 315                 320

Arg Phe Ile Met Asp Leu Val Ser Ser Leu Ser Arg Thr Tyr Lys Glu
```

```
              325                 330                 335
Ser Arg Asn Ala Phe Arg Lys Ala Leu Tyr Gly Thr Thr Ser Glu Thr
                340                 345                 350
Ala Thr Trp Arg Arg Cys Ala Asn Tyr Val Asn Gly Asn Met Glu Asn
                355                 360                 365
Ala Val Gly Arg Leu Tyr Val Glu Ala Ala Phe Ala Gly Glu Ser Lys
            370                 375                 380
His Val Val Glu Asp Leu Ile Ala Gln Ile Arg Glu Val Phe Ile Gln
385                 390                 395                 400
Thr Leu Asp Asp Leu Thr Trp Met Asp Ala Glu Thr Lys Lys Arg Ala
                405                 410                 415
Glu Glu Lys Ala Leu Ala Ile Lys Glu Arg Ile Gly Tyr Pro Asp Asp
            420                 425                 430
Ile Val Ser Asn Asp Asn Lys Leu Asn Asn Glu Tyr Leu Glu Leu Asn
                435                 440                 445
Tyr Lys Glu Asp Glu Tyr Phe Glu Asn Ile Ile Gln Asn Leu Lys Phe
        450                 455                 460
Ser Gln Ser Lys Gln Leu Lys Lys Leu Arg Glu Lys Val Asp Lys Asp
465                 470                 475                 480
Glu Trp Ile Ser Gly Ala Ala Val Val Asn Ala Phe Tyr Ser Ser Gly
                485                 490                 495
Arg Asn Gln Ile Val Phe Pro Ala Gly Ile Leu Gln Pro Pro Phe Phe
            500                 505                 510
Ser Ala Gln Gln Ser Asn Ser Leu Asn Tyr Gly Gly Ile Gly Met Val
        515                 520                 525
Ile Gly His Glu Ile Thr His Gly Phe Asp Asp Asn Gly Arg Asn Phe
    530                 535                 540
Asn Lys Asp Gly Asp Leu Val Asp Trp Trp Thr Gln Gln Ser Ala Ser
545                 550                 555                 560
Asn Phe Lys Glu Gln Ser Gln Cys Met Val Tyr Gln Tyr Gly Asn Phe
                565                 570                 575
Ser Trp Asp Leu Ala Gly Gly Gln His Leu Asn Gly Ile Asn Thr Leu
            580                 585                 590
Gly Glu Asn Ile Ala Asp Asn Gly Gly Leu Gly Gln Ala Tyr Arg Ala
        595                 600                 605
Tyr Gln Asn Tyr Ile Lys Lys Asn Gly Glu Glu Lys Leu Leu Pro Gly
    610                 615                 620
Leu Asp Leu Asn His Lys Gln Leu Phe Phe Leu Asn Phe Ala Gln Val
625                 630                 635                 640
Trp Cys Gly Thr Tyr Arg Pro Glu Tyr Ala Val Asn Ser Ile Lys Thr
                645                 650                 655
Asp Val Glu Ser Pro Gly Asn Phe Arg Ile Ile Gly Thr Leu Gln Asn
            660                 665                 670
Ser Ala Glu Phe Ser Glu Ala Phe His Cys Arg Lys Asn Ser Tyr Met
        675                 680                 685
Asn Pro Glu Lys Lys Cys Arg Val Trp
    690                 695
```

<210> SEQ ID NO 15
<211> LENGTH: 6
<212> TYPE: PRT
<213> ORGANISM: Artificial
<220> FEATURE:
<223> OTHER INFORMATION: Synthetic construct

```
<400> SEQUENCE: 15

Gly Gly Gly Gly Ser Cys
1               5
```